(12) United States Patent
Cavalli et al.

(10) Patent No.: US 9,975,861 B2
(45) Date of Patent: May 22, 2018

(54) DUAL INHIBITOR COMPOUNDS FOR USE IN THE TREATMENT OF NEURODEGENERATIVE DISORDERS AND ALZHEIMER'S DISEASE

(71) Applicants: FONDAZIONE ISTITUTO ITALIANO DI TECNOLOGIA, Genoa (IT); ALMA MATER STUDIORUM-UNIVERSITA' DI BOLOGNA, Bologna (IT)

(72) Inventors: Andrea Cavalli, Bologna (IT); Federica Prati, Genoa (IT); Giovanni Bottegoni, Genoa (IT); Angelo Danilo Favia, Genoa (IT); Daniela Pizzirani, Genoa (IT); Rita Scarpelli, Genoa (IT); Maria Laura Bolognesi, Bologna (IT)

(73) Assignees: FONDAZIONE ISTITUTO ITAIANO DI TECNOLOGIA, Genoa (IT); ALMA MATER STUDIORUM—UNIVERSITA'DI BOLOGNA, Bologna (IT)

(*) Notice: Subject to any disclaimer, the term of this patent is extended or adjusted under 35 U.S.C. 154(b) by 0 days. days.

(21) Appl. No.: 15/316,883

(22) PCT Filed: Jun. 12, 2015

(86) PCT No.: PCT/IB2015/054479
§ 371 (c)(1),
(2) Date: Dec. 7, 2016

(87) PCT Pub. No.: WO2015/189830
PCT Pub. Date: Dec. 17, 2015

(65) Prior Publication Data
US 2017/0096406 A1    Apr. 6, 2017

(30) Foreign Application Priority Data
Jun. 13, 2014 (IT) .............................. TO2014A0477

(51) Int. Cl.
| | |
|---|---|
| C07D 251/16 | (2006.01) |
| C07D 401/04 | (2006.01) |
| C07D 403/04 | (2006.01) |
| A61K 31/53 | (2006.01) |
| A61P 25/00 | (2006.01) |
| A61P 25/28 | (2006.01) |
| C07D 251/10 | (2006.01) |
| A61K 45/06 | (2006.01) |
| C07D 401/12 | (2006.01) |
| C07D 403/12 | (2006.01) |
| C07D 409/12 | (2006.01) |

(52) U.S. Cl.
CPC ............ *C07D 251/10* (2013.01); *A61K 31/53* (2013.01); *A61K 45/06* (2013.01); *C07D 401/04* (2013.01); *C07D 401/12* (2013.01); *C07D 403/12* (2013.01); *C07D 409/12* (2013.01)

(58) Field of Classification Search
CPC .. C07D 251/16; C07D 401/04; C07D 403/04; A61K 31/53
USPC .......................................... 544/220; 514/245
See application file for complete search history.

(56) References Cited

FOREIGN PATENT DOCUMENTS

| | | |
|---|---|---|
| EP | 2138488 A1 | 12/2009 |
| WO | WO-2008/015240 A1 | 2/2008 |

OTHER PUBLICATIONS

Robert Vassar, Alzheimer's Research & Therapy 2014, 6:89; BioMed Central, The Open Access Publisher pp. 1-29.*
Lahiri et al. Alzheimer's & Dementia 2014, 10, S411-S419.*
King et al. Pharmacology & Therapeutics 141 (2014) 1-12.*
Freshney, Culture of Animal Cells, A Manual of Basic Technique, Alan R. Liss, Inc., 1983, New York, p. 4.*
Dermer, Bio/Technology, 1994, 12:320.*
Elmaghraby et al. ISRN Organic Chemistry (2013) 706437, 14 pp; CA 160: 133008, 2013. CAPLUS Abstract provided.*
Bacaloglu et al. Revue Roumaine de Chimie (1972), 17(4), 747-54; CA 77: 87570, 1972. CAPLUS Abstract provided.*
Prati et al., Structure-based design and synthesis of novel bace-1GSK-3B dual inhibitors, 8th Annual Drug Discovery for Neurodegeneration Conference, Abstract (Feb. 3, 2014).
Cavalli et al., Multi-target-directed ligands to combat neurodegenerative diseases, J. Med. Chem., 51(3):347-72 (2008).
International Search Report and Written Opinion, International Application No. PCT/IB2015/054479, dated Aug. 3, 2015.

* cited by examiner

*Primary Examiner* — Venkataraman Balasubramanian
(74) *Attorney, Agent, or Firm* — Marshall, Gerstein & Borun LLP

(57) ABSTRACT

The present invention relates to Compounds of Formula (I) and pharmaceutical compositions containing the same. It further relates to their use in the prevention or treatment of central nervous system diseases or disorders, in particular, cognitive, neurodegenerative or neuronal diseases or disorders.

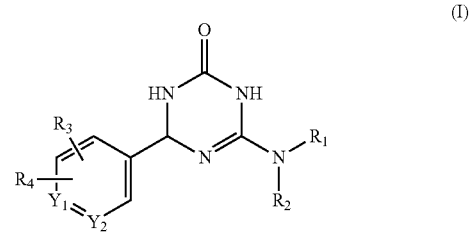

9 Claims, 11 Drawing Sheets

Figure 2A:
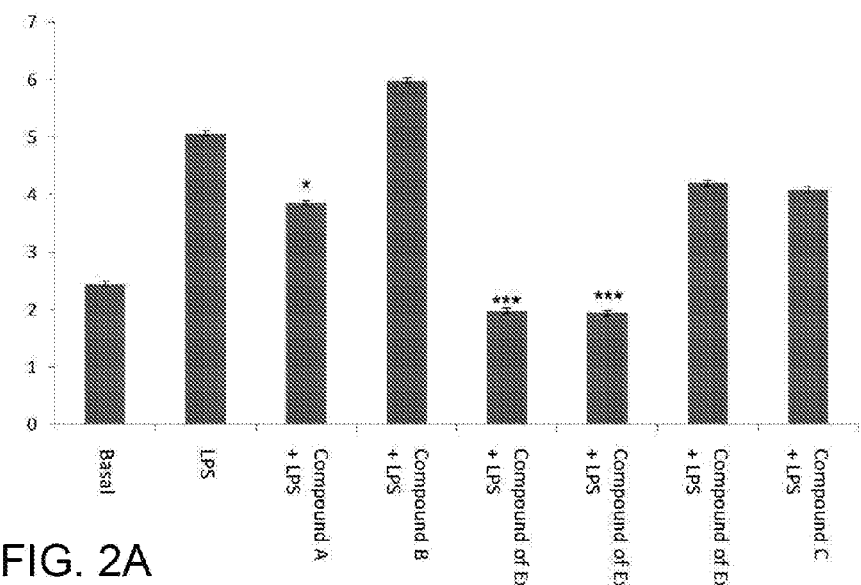

| Example | Chemical Name | Structure | M.W. | Chemical Formula |
|---|---|---|---|---|
| 1 | 4-(4-fluorophenyl)-6-(methylamino)-3,4-dihydro-1,3,5-triazin-2(1H)-one | Racemic | 222.22 | $C_{10}H_{11}FN_4O$ |
| 2 | 6-(ethylamino)-4-(o-tolyl)-3,4-dihydro-1,3,5-triazin-2(1H)-one | Racemic | 232.29 | $C_{12}H_{16}N_4O$ |
| 3 | 6-(ethylamino)-4-(4-fluorophenyl)-3,4-dihydro-1,3,5-triazin-2(1H)-one | Racemic | 236.25 | $C_{11}H_{13}FN_4O$ |
| 4 | (+)-6-(ethylamino)-4-(4-fluorophenyl)-3,4-dihydro-1,3,5-triazin-2(1H)-one | Single enantiomer | 236.25 | $C_{11}H_{13}FN_4O$ |

FIG. 1

| | | | |
|---|---|---|---|
| 5 | (−)-6-(ethylamino)-4-(4-fluorophenyl)-3,4-dihydro-1,3,5-triazin-2(1H)-one | Single enantiomer | 236.25 | $C_{11}H_{13}FN_4O$ |
| 6 | 4-(4-fluorophenyl)-6-(propylamino)-3,4-dihydro-1,3,5-triazin-2(1H)-one | Racemic | 250.27 | $C_{12}H_{15}FN_4O$ |
| 7 | 4-(4-fluorophenyl)-6-(isopropylamino)-3,4-dihydro-1,3,5-triazin-2(1H)-one | Racemic | 250.28 | $C_{12}H_{15}FN_4O$ |
| 8 | 4-(4-fluorophenyl)-6-(isobutylamino)-3,4-dihydro-1,3,5-triazin-2(1H)-one | Racemic | 264.30 | $C_{13}H_{17}FN_4O$ |
| 9 | 4-(4-fluorophenyl)-6-(phenylamino)-3,4-dihydro-1,3,5-triazin-2(1H)-one | Racemic | 284.29 | $C_{15}H_{13}FN_4O$ |

FIG. 1 - CONT.

| 10 | 6-(dimethylamino)-4-(4-fluorophenyl)-3,4-dihydro-1,3,5-triazin-2(1H)-one | Racemic | 236.25 | C₁₁H₁₃FN₄O |
| 11 | 6-(diethylamino)-4-(4-fluorophenyl)-3,4-dihydro-1,3,5-triazin-2(1H)-one | Racemic | 264.30 | C₁₃H₁₇FN₄O |
| 12 | 4-(4-fluorophenyl)-6-(piperidin-1-yl)-3,4-dihydro-1,3,5-triazin-2(1H)-one | Racemic | 276.32 | C₁₄H₁₇FN₄O |
| 13 | 6-(butylamino)-4-(4-fluorophenyl)-3,4-dihydro-1,3,5-triazin-2(1H)-one | Racemic | 264.30 | C₁₃H₁₇FN₄O |
| 14 | 6-(ethylamino)-4-(pyridin-3-yl)-3,4-dihydro-1,3,5-triazin-2(1H)-one | Racemic | 219.25 | C₁₀H₁₃N₅O |

FIG. 1 - CONT.

| | | | | |
|---|---|---|---|---|
| 15 | 4-(4-fluorophenyl)-6-(pyrrolidin-1-yl)-3,4-dihydro-1,3,5-triazin-2(1H)-one | Racemic | 262.28 | $C_{13}H_{15}FN_4O$ |
| 16 | N-(4-(4-fluorophenyl)-6-oxo-1,4,5,6-tetrahydro-1,3,5-triazin-2-yl)acetamide | Racemic | 250.23 | $C_{11}H_{11}FN_4O_2$ |
| 17 | N-(4-(4-fluorophenyl)-6-oxo-1,4,5,6-tetrahydro-1,3,5-triazin-2-yl)-2-propylpentanamide | Racemic | 334.40 | $C_{17}H_{23}FN_4O_2$ |
| 18 | 5-(1,2-dithiolan-3-yl)-N-(4-(4-fluorophenyl)-6-oxo-1,4,5,6-tetrahydro-1,3,5-triazin-2-yl)pentanamide | Racemic | 396.50 | $C_{17}H_{21}FN_4O_2S_2$ |
| 19 | 3-((1H-benzo[d][1,2,3]triazol-1-yl)oxy)-N-(4-(4-fluorophenyl)-6-oxo-1,4,5,6-tetrahydro-1,3,5-triazin-2-yl)propanamide | Racemic | 397.37 | $C_{18}H_{16}FN_7O_3$ |

FIG. 1 - CONT.

| 20 | N-(4-(4-fluorophenyl)-6-oxo-1,4,5,6-tetrahydro-1,3,5-triazin-2-yl)-2-phenoxyacetamide | Racemic | 342.33 | $C_{17}H_{15}FN_4O_3$ |
| 21 | 2-(4-fluorophenoxy)-N-(4-(4-fluorophenyl)-6-oxo-1,4,5,6-tetrahydro-1,3,5-triazin-2-yl)acetamide | Racemic | 360.32 | $C_{17}H_{14}F_2N_4O_3$ |

FIG. 1 - CONT.

| | | | |
|---|---|---|---|
| 22 | 6-((3-(dimethylamino)propyl)amino)-4-(4-fluorophenyl)-3,4-dihydro-1,3,5-triazin-2(1H)-one | 293.35 | $C_{14}H_{20}FN_5O$ |
| 23 | 4-(4-fluorophenyl)-6-((3-(piperidin-1-yl)propyl)amino)-3,4-dihydro-1,3,5-triazin-2(1H)-one | 333.41 | $C_{17}H_{24}FN_5O$ |
| 24 | 6-(benzylamino)-4-(4-fluorophenyl)-3,4-dihydro-1,3,5-triazin-2(1H)-one | 298.32 | $C_{16}H_{15}FN_4O$ |

FIG. 1 - CONT.

| | | | |
|---|---|---|---|
| 25 | 4-(4-fluorophenyl)-6-((pyridin-4-ylmethyl)amino)-3,4-dihydro-1,3,5-triazin-2(1H)-one | 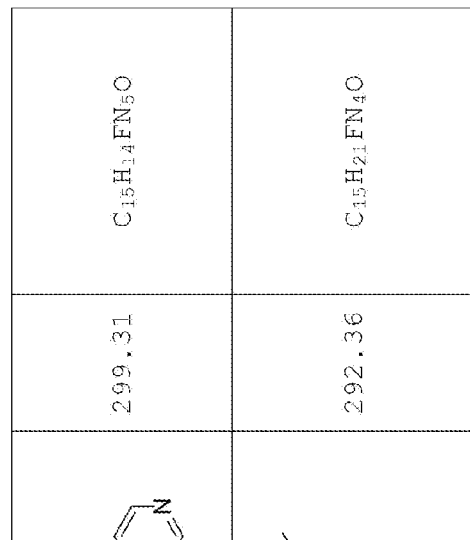 Racemic | 299.31 | $C_{15}H_{14}FN_5O$ |
| 26 | 6-(dipropylamino)-4-(4-fluorophenyl)-3,4-dihydro-1,3,5-triazin-2(1H)-one | 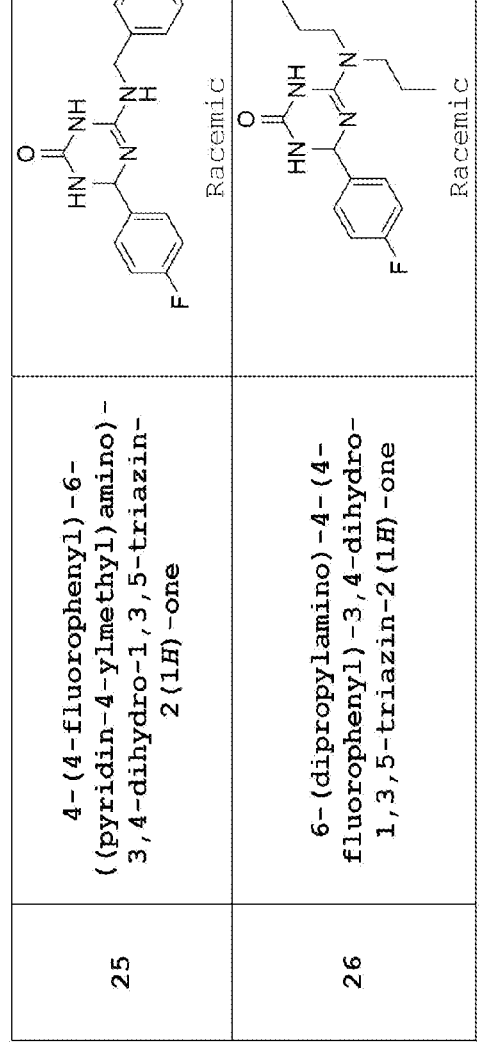 Racemic | 292.36 | $C_{15}H_{21}FN_4O$ |
FIG. 1 - CONT.

DUAL INHIBITOR COMPOUNDS FOR USE IN THE TREATMENT OF NEURODEGENERATIVE DISORDERS AND ALZHEIMER'S DISEASE

CROSS-REFERENCE TO RELATED APPLICATIONS

This is the U.S. national phase of International Application No. PCT/IB2015/054479, filed Jun. 12, 2015, which claims the benefit of Italian Patent Application No. TO2014A000477, filed Jun. 13, 2014.

TECHNICAL FIELD

The present invention relates to novel triazinone derivatives and their use as therapeutic agents to treat a variety of neurodegenerative disorders, including Alzheimer's disease (AD).

BACKGROUND ART

AD is a progressive neurological disorder characterized by deterioration of cognitive function, dementia, memory loss, and altered behavior.

AD is the major unmet medical need in neurology, and it is estimated that, by 2050, there could be more than 100 million AD patients worldwide [Alzheimer's Association, 2013 Alzheimer's disease facts and figures. Alzheimer's & Dementia 2013, 9, 208-45]. AD dramatically affects the quality of life of the sufferers and their families, and despite massive investments, there are few, if any, effective treatments for AD.

The AD pathogenesis involves a complex interplay of genetic and biochemical factors, including an increased production of β-amyloid peptide (amyloid hypothesis) and an increased phosphorylation of the microtubule-associated tau protein (tau hypothesis) [Querfurth, H. W. and LaFerla, F. M. Mechanisms of disease: Alzheimer's disease. N Engl J Med 2010, 362, 329-44]. The β-amyloid peptide (Aβ) is generated by the amyloidogenic cleavage of the membrane-associated amyloid precursor protein. Two major enzymes have been identified as responsible for Aβ, formation, namely β-secretase (BACE-1) and γ-secretase. Huge efforts have been devoted to the identification of small molecule inhibitors of either these enzymes. γ-secretase inhibitors have reached phase III of clinical trial but they failed because of lack of efficacy and heavy side effects (i.e. skin cancer) [Blennow, K.; Zetterberg, H.; Haass, C.; Finucane, T. Semagacestat's fall: where next for AD therapies? Nat Med 2013, 19, 1214-15].

BACE-1 inhibitors are still in clinical development, with the most advanced compounds in phase III of clinical trial. BACE-1 remains one of the few target options available for a potentially efficacious treatment within the amyloid hypothesis of AD [Rafii, M. S. Update on Alzheimer's disease therapeutics. Rev Recent Clin Trials 2013, 8, 110-18].

As for the tau hypothesis, research activities have been focused on the identification of kinase inhibitors, as a few kinases have been identified as responsible for the tau phosphorylation. Among these enzymes, glycogen-synthase kinase 3β(GSK-3β) has been identified as one of the key players within this pathological cascade. GSK-3β is responsible for tau hyperphosphorylation, which causes tau to be detached from the microtubules and precipitate as intraneuronal tangle aggregates [Avila, J.; Wandosell, F.; Hernandez, F. Role of glycogen synthase kinase-3 in Alzheimer's disease pathogenesis and glycogen synthase kinase-3 inhibitors. Expert Rev Neurother 2010, 10, 703-10]. Furthermore, GSK-3β has been proposed as a possible link between β-amyloid peptide and tau protein [Hernández, F.; Gómez de Barreda, E.; Fuster-Matanzo, A.; Lucas, J. J.; Avila, J. GSK3: a possible link between beta amyloid peptide and tau protein. Exp Neurol. 2010, 223, 322-25]. Therefore, GSK-3β inhibitors have been long sought [Martinez, A.; Perez, D. I.; Gil, C. Lessons learnt from glycogen synthase kinase 3 inhibitors development for Alzheimer's disease. Curr Top Med Chem 2013; 13, 1808-19].

Despite the two hypotheses have been considered in contrast, recent evidences suggest that AD is a multifactorial disease, where several neurodegenerative pathways can concomitantly contribute to neuronal death and associated neurodegeneration [Ittner, L. M.; Götz, J. Amyloid-β and tau a toxic pas de deux in Alzheimer's disease. Nat Rev Neurosci 2011, 12, 65-72].

In this scenario, multitarget drugs (MTDs), namely small organic molecules able to hit multiple targets affecting different pathological pathways, are emerging as promising disease-modifying compounds for the treatment of complex neurological disorders [Cavalli, A.; Bolognesi, M. L.; Minarini, A.; Rosini, M.; Tumiatti, V.; Recanatini, M.; Melchiorre, C. Multi-target-directed ligands to combat neurodegenerative diseases. J Med Chem 2008, 51, 347-72. Bolognesi, M. L.; Simoni, E.; Rosini, M.; Minarini, A.; Tumiatti, V.; Melchiorre, C. Multitarget-directed ligands: innovative chemical probes and therapeutic tools against Alzheimer's disease. Curr Top Med Chem 2011, 11, 2797-806].

The strategy of targeting two or more proteins at the same time with a single compound can provide therapeutic effects superior to those of a selective drug.

This can be explained by the number of potential benefits offered by the use of MTDs over cocktails or multicomponent drugs. The advantages of MTDs can be summarized as follows: 1) reduced uncertainty in clinical development since predicting the pharmacokinetics of a single compound is much easier than with a drug cocktail, overcoming the problem of different bioavailability, pharmacokinetics and metabolism; 2) certainty on the pharmacodynamics; 3) improved efficacy due to the synergistic effect of simultaneously inhibiting multiple targets; 4) improved safety by decreasing the side effects related to the load of a drug cocktail (reduced risk of drug-drug interactions); this is particularly relevant for drug metabolism, where the competition of different drugs for the same metabolic enzyme affect their toxicity. All these considerations are of particular relevance as one of the major contributions to attrition rate in drug development continues to be the drug candidate's pharmacokinetic profiling.

Another important advantage is a simplified therapeutic regimen and improved compliance, which is particularly important for elderly AD patients and their caregivers [Small, G.; Dubois, B. A review of compliance to treatment in Alzheimer's disease: potential benefits of a transdermal patch. Curr Med Res Opin 2007, 23, 2705-2713]. With this regard, a key issue is that AD patients are susceptible to a wide range of concomitant medical conditions (comorbidity), including hypertension, vascular diseases, and diabetes, which can often be associated. Thus, problems associated with polypharmacy in the geriatric population have been recognized as critical in recent years. These problems primarily consist of drug interactions which occur more frequently in this population because of the co-existence of chronic disease and impaired organ functions. Two drugs that themselves are safe cannot be assumed to be safe in combination, particularly in elderly patients. It follows that the number of drugs administered simultaneously should be reduced as much as possible, since advanced age is an unpredictable risk factor for drug treatment [Turnheim, K. When drug therapy gets old: pharmacokinetics and pharmacodynamics in the elderly. Exp Geront 2003, 38, 843-853]. As such, MTDs are strongly favored over combination therapy with respect to the complexity of interactions between polypharmacy, comorbidity, altered pharmacodynamic sensitivity, and changes in pharmacokinetics in the elderly. The clinical use of MTDs can also simplify the therapeutic regimen [Youdim, M. B., and Buccafusco, J. J. CNS Targets for multifunctional drugs in the treatment of Alzheimer's and Parkinson's diseases. J Neural Transm 2005, 112, 519-537]. Compliance with prescribed medication regimens is essential for effective treatment. Non-compliance represents a general problem, but is especially challenging for forgetful AD patients and their caregivers [Small, G., and Dubois, B. A review of compliance to treatment in Alzheimer's disease: potential benefits of a transdermal patch. Curr Med Res Opin 2007, 23, 2705-2713]. Consequently, a simplified MTD regimen may increase treatment adherence. All the above mentioned advantages are not available with drug cocktails.

The multitarget ligand strategy is an innovative approach to the development of novel drug candidates for the treatment of complex neurological disorders, especially in view of the fact that the major basic processes involved in neurodegenerative diseases are multifactorial in nature [Cavalli, A.; Bolognesi, M. L.; Minarini, A.; Rosini, M.; Tumiatti, V.; Recanatini, M.; Melchiorre, C. Multi-target-directed ligands to combat neurodegenerative diseases. J Med Chem 2008, 51, 347-72]. Such a strategy is thus based on the concept that a single multifunctional compound can be deployed to hit multiple targets that cooperate in the neurodegenerative process underlying AD and other neurodegenerative diseases, and therefore would prevent unwanted compensation among interacting pathogenic pathways. Indeed, the multitarget compounds could represent a practical alternative to the use of drug combinations. Since most of the neurodegenerative mechanisms are shared by many neuronal disorders, such multitarget compounds may also be used as medications for other illnesses.

One problem connected to multitarget compounds is that many of them are inefficient in terms of their binding energy per unit of molecular weight. This is because they contain groups that are only important for one of the targets, being merely tolerated by the others. This results in an unbalanced profile [Morphy, R., and Rankovic, Z. Fragments, network biology and designing multiple ligands. Drug Discov Today 2007, 12, 156-160; Morphy, R. The influence of target family and functional activity on the physicochemical properties of pre-clinical compounds. J Med Chem 2006, 49, 2969-2978]. The consequent optimization of activities is not an easy task. In fact, a multitarget compound is to be considered as a new chemical entity, with its own pharmacological profile, therefore its efficacy on the targets is not predictable a priori, and the complete process of drug development must be faced.

In the context of MTDs, just to name a few, we could mention memoquin, disclosed a few years ago by Cavalli and coworkers [Cavalli, A.; Bolognesi, M. L.; Capsoni, S.; Andrisano, V.; Bartolini, M.; Margotti, E.; Cattaneo, A.; Recanatini M.; Melchiorre, C. A small molecule targeting the multifactorial nature of Alzheimer's disease. Chem Int Ed Engl 2007, 46, 3689-92], and ladostigil developed by Youdim and coworkers and currently in phase II of clinical trial [Weinreb, O.; Mandel, S.; Bar-Am, O.; Yogev-Falach, M.; Avramovich-Tirosh, Y.; Amit, T.; Youdim, M. B. Multifunctional neuroprotective derivatives of rasagiline as anti-Alzheimer's disease drug. Neurotherapeutics 2009, 6, 163-74].

WO 2008/015240 discloses a family of N-phenyl-prenylamine derivatives and claims their use to treat cognitive, neurodegenerative or neuronal diseases or disorders, such as Alzheimer's disease or Parkinson's disease; in in vitro assays, they were shown to exhibit a mild to moderate inhibitory effect on the enzymatic targets GSK-3β and only a few of them also on BACE.

EP2138488 A1 discloses 4-(pyridin-4-yl)-1H-[1,3,5]-triazin-2-one derivatives as selective GSK-3β inhibitors for the treatment of neurodegenerative diseases; in addition to be single target inhibitors, the compounds described therein are aromatic in character and display a planar geometry of the triazinone core scaffold, in which the carbon atom at position 4 of the triazinone ring that bears the pyridine ring is sp2-hybridized and is therefore unable to form stereoisomers. Consequently, the compounds of EP2138488 are achiral compounds.

In multitarget drug discovery, fragment-based approaches have been reported to play a pivotal role. In fact, fragments, rather than lead-like compounds, may have the ability to bind more than a single target [Hann, M. M.; Leach, A. R.; Harper, G. Molecular complexity and its impact on the probability of finding leads for drug discovery. J Chem Inf Comput Sci 2001, 41, 856-64. Bottegoni, G.; Favia, A. D.; Recanatini, M.; Cavalli, A. The role of fragment-based and computational methods in polypharmacology. Drug Discov Today 2012, 17, 23-34]. Then, in the fragment-to-lead step, one should carefully maintain the desired biological profile against the pathological targets, while avoiding potential liability due to off-target binding.

On these premises, a fragment-based approach has been used to design small molecules able to inhibit BACE-1 and GSK-3β enzymes, two validated targets within the two major pathological cascades of AD. Remarkably, these enzymes are ancestrally quite divergent with a sequence identity of 19%, close to the random limit. To design dual-inhibitors, a ligand-based approach has been used, combining those pharmacophoric features responsible for binding to BACE-1 and GSK-3β, such as a guanidino motif and a cyclic amide group respectively and, subsequently, docking simulations aimed at studying the interactions of the newly designed compounds into the catalytic pocket of both enzymes.

A series of 4-phenyl-6-amino-3,4-dihydro-1,3,5-triazin-2 (1H)-ones turned out to be a scaffold bearing the required chemical features for binding to both targets [Prati F. et al., Structure-based design and synthesis of novel BACE-1/ GSK-3β dual inhibitors. 8th Annual drug discovery conference for neurodegeneration. Feb. 2-4, 2014, Miami, Fla.].

Synthesis, identification by physical and spectral data, and associated physico-chemical properties of 4-phenyl-6-amino-3,4-dihydro-1,3,5-triazin-2(1H)-ones variously substituted at the 4-phenyl ring are described in several literature publications [Ostrogovich A., Gazzetta Chimica Italiana 1909, 39 i, 540; Ostrogovich A., Median V. B., Gazzetta Chimica Italiana 1929, 59, 181-198; Ostrogovich A., Median V. B., Gazzetta Chimica Italiana 1929, 59, 198-200; Ostrogovich A., Median V. B., Gazzetta Chimica Italiana 1934, 64, 792-800; Wakabayashi k., Okuzu M., Nippon Dojo Hiryogaku Zasshi 1970, 41(6), 237-245; Bacaloglu R.

et al. Revue Roumaine de Chimie 1972, 17(4), 747-754; Neamtiu et al., Zeitschrift fuer Physikalische Chemie (Leipzig) 1976, 257, 1089-1090; Gorbatenko V. I., et al., Zhurnal Organicheskoi Khimii 1976, 12(nb.10), 2103-2107].

However, these molecules have not been considered satisfactory from the neuroprotective and neurogenesis standpoints.

There is the need in the art to find new MTDs to treat Alzheimer's disease.

DISCLOSURE OF INVENTION

The aim of the present invention is therefore to provide novel compounds having a large spectrum of neuroprotective and anti-neurodegenerative properties and able to be effective in the treatment of AD. In particular, one of the aim of the present invention is to provide novel compounds having inhibitory activity against BACE-1 and GSK-3β demonstrating an increased neuroprotective and neurogenesis activity to treat Alzheimer's disease.

The aforementioned objective has been met according to compounds of claim 1, to a pharmaceutical composition of claim 7, to the uses of claims 10 and 11. Preferred embodiments are set out within the dependent claims.

In particular, the inventors have now identified a novel series of 4-aryl-6-amino-3,4-dihydro-1,3,5-triazin-2(1H)-ones that, differently from the compounds disclosed in the prior art, are capable to inhibit both the BACE-1 and GSK-3β enzymes with an increased effective pharmacological effect, and possess a non-planar geometry in which the carbon atom at position 4 of the triazinone ring is sp3-hybridized. Such modification give rise to a higher degree of conformational freedom, including the possibility to generate the corresponding enantiomers. In addition, differently from the compounds of the prior art, the compounds of the present invention are characterized by the presence of a secondary or tertiary amino group, or a secondary or tertiary amide group, at position $C_6$ of the 3,4-dihydro-1,3,5-triazin-2(1H)-one ring which, unexpectedly, demonstrated a superior neuroprotective and neurogenesis activity in a pharmacological model of neuroinflammation in astraglia and microglia in comparison with the corresponding known primary amines.

This novel series of compounds has been further investigated in terms of structure-activity relationships (SARs) against BACE-1 and GSK-3β, by synthesizing and testing a number of novel exemplified compounds for their inhibitory activity against the two enzymes.

The following paragraphs provide definitions of the various chemical moieties of the compounds according to the invention and are intended to apply uniformly through-out the specification and claims unless an otherwise expressly set out definition provides a broader definition.

The term "alkyl", as used herein by itself or as a part of another substituent, refers to aliphatic hydrocarbon groups. Such term includes linear (unbranched) chains or branched chains, which may be fully saturated, mono- or polyunsaturated.

The term "unsaturated" aliphatic hydrocarbon group encompasses alkenyl and alkynyl.

The term "alkenyl", as used herein, refers to alkyl groups, preferably having from 2 to 6 carbon atoms and containing at least one carbon-carbon double bond.

The term "alkynyl", as used herein, refers to alkyl groups, preferably having from 2 to 6 carbon atoms and containing at least one carbon-carbon triple bond.

Non-limiting examples of alkyl groups according to the invention are, for example, methyl, ethyl, propyl, isopropyl, n-butyl, iso-butyl, tert-butyl, n-pentyl, iso-pentyl, n-hexyl, ethenyl, 1-propenyl, 2-propenyl, 1- or 2-butenyl, ethynyl, 1-propynyl, 2-propynyl, 1- or 2-butynyl and the like.

Alkyl groups according to the present invention may be unsubstituted or substituted by one or more substituents.

The term "cycloalkyl", as used herein, refers to a saturated or partially unsaturated carbocyclic group having a single ring. It includes cycloalkenyl groups.

Non-limiting examples of cycloalkyl groups according to the invention are, for example, cyclopropane, cyclobutane, cyclopentane, cyclohexane, cycloheptane, cyclopentene, cyclohexene, cyclohexadiene and the like.

Cycloalkyl groups according to the present invention may be unsubstituted or substituted by one or more substituents.

The term "heteroalkyl", as used herein, refers to an alkyl group, as defined above, that is linked to the remainder of the compound via a heteroatom or, alternately, an alkyl group wherein at least one carbon atom is replaced by a heteroatom. Heteroalkyl groups can be unsubstituted or substituted by one or more substituents.

The term "heterocycloalkyl" group, ("non-aromatic heterocycle" group), refers to a cycloalkyl group (non aromatic group) wherein at least one of the carbon atoms has been replaced by a heteroatom selected from nitrogen, oxygen and sulfur. Heterocycloalkyl groups can be unsubstituted or substituted.

As used herein, the term "heteroatom" refers to an atom other than carbon or hydrogen. Heteroatom typically is meant to include oxygen (O), nitrogen (N), and sulfur (S). The heteroatom as used herein may optionally be oxidized and the nitrogen heteroatom may optionally be quaternized.

Non-limiting examples of heteroalkyl groups according to the invention are, for example, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—CH=NOCH$_3$, and —CH=CH—N($CH_3$)—$CH_3$. Up to two heteroatoms may be consecutive, such as, for example, —$CH_2$—NH—OCH$_3$.

Examples of heterocycloalkyls include, but are not limited to, lactams, lactones, cyclic imides, cyclic thioimides, cyclic carbamates, 1-(1,2,5,6-tetrahydropyridyl), tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl), trioxane, hexahydro-1,3,5-triazine, tetrahydrothiophene, tetrahydrofuran (tetrahydrofuran-2-yl, tetrahydrofuran-3-yl), 1,2-dithiolan-3-yl, pyrroline, pyrrolidine, pyrrolidone, pyrrolidinone, pyrazoline, pyrazolidine, imidazoline, imidazolidine, 1,3 dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "alkoxy", as used herein, refers to an alkyl group that is linked to the remainder of the compound by an oxygen atom.

The term "halogen", as used herein, refers to fluorine, chlorine, bromine and iodine.

The term "haloalkyl," as used therein refers to monohaloalkyl and polyhaloalkyl groups. For example, the term "halo($C_{1-6}$)alkyl" is meant to include, but not be limited to, the fluoro$C_{1-6}$alkyl, such as trifluoromethyl, 2,2,2-trifluoroethyl, and the like.

The term "haloalkoxy," as used therein refers to monohaloalkoxy and polyhaloalkoxy groups. For example, the term "halo($C_{1-6}$)alkoxy" is meant to include, but not be limited to, the fluoro$C_{1-6}$alkoxy, such as trifluoromethoxy, 2,2-difluoromethoxy, and the like.

The term "aryl", as used herein, refers to a hydrocarbon consisting of an unsubstituted or substituted mono-, bi- or tricarbocyclic ring system, wherein the rings are fused together and at least one of the carbocyclic ring is aromatic. The term "aryl" means for example a cyclic aromatic such as a 6-membered hydrocarbon ring, a two six-membered fused hydrocarbon rings. Non-limiting examples of aryl groups are, for example, phenyl, alpha- or beta-naphthyl, 9,10-dihydroanthracenyl, indanyl, fluorenyl and the like. Aryl groups according to the present invention may be unsubstituted or substituted by one or more substituents.

The term "heteroaryl", as used herein, refers to an aryl as defined above wherein one to four carbon atoms are independently replaced by heteroatoms chosen from the group consisting of nitrogen, oxygen and sulfur. Non-limiting examples of heteroaryl groups are, for example, pyrrolyl, furyl, thiophenyl, imidazolyl, pyrazolyl, oxazolyl, isoxazolyl, triazolyl, isothiazolyl, indolyl, benzofuranyl, benzothiophenyl, benzimidazolyl, benzopyrazolyl, benzo[d][1,2,3]triazol-1-yl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl. Heteroaryl groups according to the present invention may be unsubstituted or substituted by one or more substituents.

The term "aromatic ring", as used herein, refers to a moiety wherein the constituent carbon atoms make up an unsaturated ring system, all atoms in the ring system are $sp^2$ hybridized and the total number of n-electrons is equal to 4n+2, wherein n is an integer.

The term "heteroaromatic ring", as used herein, refers to an "aromatic ring" as defined above wherein one or more carbon atoms are independently replaced by heteroatoms chosen from the group consisting of nitrogen, oxygen and sulfur.

Unless otherwise indicated, the term "substituted", as used herein, means that one or more hydrogen atoms of the above mentioned groups are replaced with another non-hydrogen atom or functional group, provided that normal valencies are maintained and that the substitution results in a stable compound. In particular, according to the present invention the non-hydrogen atom or functional group are selected from the group consisting of alkyl, substituted alkyl, aryl, substituted aryl, arylalkyl, alkoxy, cycloalkyloxy, aryloxy, arylalkyloxy, hydroxy, heteroaryl, heteroaryloxy, heterocyclyloxy, trifluoromethyl, trifluoromethoxy, carboxy, acyl, aroyl, heteroaroyl, halogen, nitro, cyano, alkoxycarbonyl, aryloxycarbonyl, aralkyloxycarbonyl, cycloalkyloxycarbonyl, heteroaryloxycarbonyl, acyloxy, alkylthio, arylthio, alkylsulfinyl, arylsulfinyl, alkylsulfonyl, arylsulfonyl, —O-aroyl, —O-heteroaroyl, oxo (=O), —C(=O)—$NR^hR^k$, and —$NR^pR^q$, wherein each of $R^h$, $R^k$, $R^p$, and $R^q$ independently represents hydrogen, unsubstituted or substituted alkyl, unsubstituted or substituted cycloalkyl, unsubstituted or substituted aryl, unsubstituted or substituted arylalkyl, unsubstituted or substituted heteroaryl, unsubstituted or substituted heterocyclyl, acyl, aroyl, heteroaroyl, and when $R^h$ and $R^k$, or $R^p$ and $R^q$ are taken together with the nitrogen atom to which they are bound, the group —$NR^hR^k$ or the group $NR^pR^q$ represent a heterocyclyl residue and wherein the terms alkyl, cycloalkyl, aryl, heteroaryl, heterocyclyl are as above defined.

The term "pharmaceutically acceptable salts" refers to salts of the below identified compounds of Formula (I) that retain the desired biological activity and are accepted by regulatory authorities.

As used herein, the term "salt" refers to any salt of a compound according to the present invention prepared from an inorganic or organic acid or base and internally formed salts. Typically, such salts have a physiologically acceptable anion or cation.

Furthermore, the compounds of Formula (I) may form an acid addition salt or a salt with a base, depending on the kind of the substituents, and these salts are included in the present invention, as long as they are pharmaceutically acceptable salts.

Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, trifluoroacetic acid, oxalic acid, tartaric acid, succinic acid, malic acid, fumaric acid, maleic acid, ascorbic acid, benzoic acid, alginic acid, polyglutamic acid and naphthalene sulfonic acid. The hydrochloric salt is preferred.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (I) using conventional methods.

The terms "derivative" and "derivatives" refer to each of the compounds of Formula (I) and are meant to include their pharmaceutically acceptable hydrates, solvates, crystalline forms, isotopically-labelled derivatives, tautomers, geometrical or optical isomers, stereoisomers, pharmaceutically active derivatives and also any suitable forms as illustrated hereinafter.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (I) may readily be isolated in association with solvent molecules by crystallization or evaporation of an appropriate solvent to give the corresponding solvates.

The compounds of Formula (I) may be in crystalline form. In certain embodiments, the crystalline forms of the compounds of Formula (I) are polymorphs.

The subject invention also includes isotopically-labelled compounds, which are identical to those recited in Formula (I) and following, but differ for the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, phosphorous, sulfur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (Positron Emission Tomography), and $^{125}$I isotopes are particularly useful in SPECT (Single Photon Emission Computerized Tomography), all useful in brain imaging. Furthermore, substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. Isotopically-labelled compounds of Formula (I) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (I) may exist in the form of other tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (I) may have asymmetric carbon atoms or axial asymmetries in some cases and, correspondingly, it may exist in the form of optical isomers such as an (R)-form, an (S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formula (I) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist.

The term "pharmaceutically active derivative" refers to any compound derived from the compounds of Formula (I) that upon administration to the recipient, is capable of providing directly or indirectly, the activity disclosed herein.

The present invention also encompasses active metabolites of compounds of Formula (I).

According to a first aspect of the invention, compounds of Formula (I)

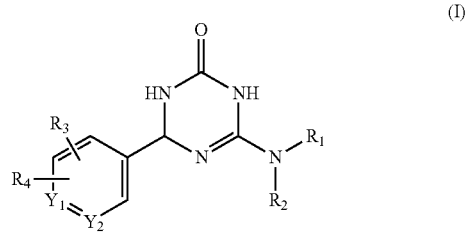

or pharmaceutically acceptable salts or solvates thereof are provided.

In the compounds of Formula (I):

$R_1$ is hydrogen, linear or branched, unsubstituted or substituted, $C_{1-6}$ alkyl;

$R_2$ is selected from the group consisting of linear or branched, unsubstituted or substituted, $C_{1-6}$alkyl, $C_{2-6}$ alkenyl, $C_{2-6}$alkynyl, unsubstituted or substituted $C_{3-6}$ cycloalkyl, unsubstituted or substituted $C_{3-6}$cycloalkyl$C_{1-6}$ alkyl, unsubstituted or substituted aryl, unsubstituted or substituted heteroaryl, unsubstituted or substituted aryl $C_{1-6}$alkyl, unsubstituted or substituted aryloxy$C_{1-6}$alkyl, unsubstituted or substituted heteroaryl$C_{1-6}$alkyl, unsubstituted or substituted heteroaryloxy$C_{1-6}$alkyl, unsubstituted or substituted heterocycloalkyl$C_{1-6}$alkyl, COR$_5$;

$R_5$ is selected from the group consisting of linear or branched unsubstituted or substituted $C_{1-9}$alkyl, unsubstituted or substituted $C_{3-6}$cycloalkyl, unsubstituted or substituted $C_{3-6}$cycloalkyl$C_{1-6}$alkyl, unsubstituted or substituted aryl, unsubstituted or substituted heteroaryl, unsubstituted or substituted aryl$C_{1-6}$alkyl, unsubstituted or substituted aryloxy$C_{1-6}$alkyl, unsubstituted or substituted heteroaryl$C_{1-6}$ alkyl, unsubstituted or substituted heteroaryloxy$C_{1-6}$alkyl, unsubstituted or substituted heterocycloalkyl$C_{1-6}$alkyl.

Alternately, $R_1$ and $R_2$ together with the nitrogen atom to which they are attached may form a 4- to 7-membered azacyclic ring containing up to three heteroatoms selected from nitrogen and oxygen.

$Y_1$ and $Y_2$ are independently selected from C or N.

$R_3$ and $R_4$ are independently selected from the group consisting of hydrogen, halogen, linear or branched unsubstituted or substituted $C_{1-6}$alkyl, unsubstituted or substituted $C_{1-6}$alkoxy, unsubstituted or substituted hydroxy$C_{1-6}$alkyl, hydroxy, cyano, nitro, unsubstituted or substituted fluoro $C_{1-6}$alkyl, unsubstituted or substituted fluoro$C_{1-6}$alkoxy, amino, monoalkylamino, dialkylamino.

According to a first embodiment:

$R_1$ is hydrogen or linear $C_{1-6}$alkyl, unsubstituted or substituted with one or more $R_6$ substituents;

$R_2$ is selected from the group consisting of linear or branched $C_{1-6}$alkyl, unsubstituted or substituted with one or more $R_6$ substituents; $C_{3-6}$cycloalkyl, unsubstituted or substituted with one or more $R_6$ substituents; $C_{3-6}$cycloalkyl$C_{1-6}$ alkyl, unsubstituted or substituted with one or more $R_6$ substituents; aryl, unsubstituted or substituted with one or more $R_6$ substituents; heteroaryl, unsubstituted or substituted with one or more $R_6$ substituents; aryl$C_{1-6}$alkyl, unsubstituted or substituted with one or more $R_6$ substituents; aryloxy$C_{1-6}$alkyl, unsubstituted or substituted with one or more $R_6$ substituents; heteroaryl$C_{1-6}$alkyl, unsubstituted or substituted with one or more $R_6$ substituents; heteroaryloxy$C_{1-6}$alkyl, unsubstituted or substituted with one or more $R_6$ substituents; heterocycloalkyl$C_{1-6}$alkyl, unsubstituted or substituted with one or more $R_6$ substituents; or COR$_5$;

$R_5$ is selected from the group consisting of linear or branched $C_{1-9}$alkyl, unsubstituted or substituted with one or more $R_6$ substituents; $C_{3-6}$cycloalkyl, unsubstituted or substituted with one or more $R_6$ substituents; $C_{3-6}$cycloalkyl$C_{1-6}$ alkyl, unsubstituted or substituted with one or more $R_6$ substituents; aryl, unsubstituted or substituted with one or more $R_6$ substituents; heteroaryl, unsubstituted or substituted with one or more $R_6$ substituents; aryl$C_{1-6}$alkyl, unsubstituted or substituted with one or more $R_6$ substituents; aryloxy$C_{1-6}$alkyl, unsubstituted or substituted with one or more $R_6$ substituents; heteroaryl$C_{1-6}$alkyl, unsubstituted or substituted with one or more $R_6$ substituents; heteroaryloxy$C_{1-6}$alkyl, unsubstituted or substituted with one or more R$_6$ substituents; heterocycloalkylC$_{1-6}$alkyl, unsubstituted or substituted with one or more R$_6$ substituents;

R$_6$ is selected from the group consisting of halogen, hydroxy, alkoxy, amino, monoalkylamino, dialkylamino.

Alternately, R$_1$ and R$_2$ together with the nitrogen atom to which they are attached may form a 4- to 7-membered azacyclic ring containing up to two nitrogen atoms.

Y$_1$ and Y$_2$ are independently selected from C or N;

R$_3$ and R$_4$ are independently selected from the group consisting of hydrogen, halogen, linear or branched unsubstituted or substituted C$_{1-6}$alkyl, unsubstituted or substituted C$_{1-6}$alkoxy, hydroxy, trifluoromethyl, amino, monoalkylamino, dialkylamino.

According to a second embodiment:

R$_1$ is hydrogen or linear C$_{1-4}$alkyl, unsubstituted or substituted with one or more R$_6$ substituents;

R$_2$ is selected from the group consisting of linear or branched C$_{1-4}$alkyl, unsubstituted or substituted with one or more R$_6$ substituents; C$_{3-6}$cycloalkyl, unsubstituted or substituted with one or more R$_6$ substituents; C$_{3-6}$cycloalkylC$_{1-4}$ alkyl, unsubstituted or substituted with one or more R$_6$; aryl, unsubstituted or substituted with one or more R$_6$ substituents; heteroaryl, unsubstituted or substituted with one or more R$_6$ substituents; arylC$_{1-4}$alkyl, unsubstituted or substituted with one or more R$_6$ substituents; heteroarylC$_{1-4}$ alkyl, unsubstituted or substituted with one or more R$_6$ substituents; heterocycloalkylC$_{1-4}$alkyl, unsubstituted or substituted with one or more R$_6$ substituents; or COR$_5$;

R$_5$ is selected from the group consisting of linear or branched C$_{1-7}$alkyl, unsubstituted or substituted with one or more R$_6$ substituents; arylC$_{1-4}$alkyl, unsubstituted or substituted with one or more R$_6$ substituents; aryloxyC$_{1-4}$alkyl, unsubstituted or substituted with one or more R$_6$ substituents; heteroarylC$_{1-4}$alkyl, unsubstituted or substituted with one or more R$_6$ substituents; heteroaryloxyC$_{1-4}$alkyl, unsubstituted or substituted with one or more R$_6$ substituents; heterocyclylC$_{1-4}$alkyl, unsubstituted or substituted with one or more R$_6$ substituents;

R$_6$ is selected from the group consisting of halogen, amino, monoalkylamino, dialkylamino.

In particular R$_6$ can be selected from the group consisting of halogen, dialkylamino.

Alternately, R$_1$ and R$_2$ together with the nitrogen atom to which they are attached may form a 4- to 6-membered azacyclic ring containing one nitrogen atom.

Y$_1$ and Y$_2$ are independently selected from C or N;

R$_3$ and R$_4$ are independently selected from the group consisting of hydrogen, halogen, linear or branched unsubstituted or substituted C$_{1-3}$alkyl, unsubstituted or substituted C$_{1-3}$alkoxy, hydroxy, trifluoromethyl.

According to a third embodiment:

R$_1$ is hydrogen, methyl, ethyl and n-propyl, unsubstituted or substituted with one R$_6$ substituent;

R$_2$ is selected from the group consisting of methyl, ethyl, n-propyl, i-propyl, n-butyl, i-butyl, cyclopropyl, cyclopropylmethyl, phenyl, benzyl, 4-pyridylmethyl, piperidin-1-ylpropyl, morpholin-4-yl-propyl, 4-methylpiperazin-1-yl-propyl, or COR$_5$;

R$_5$ is selected from the group consisting of methyl, ethyl, n-propyl, i-propyl, i-butyl, 1-propylbutyl, phenoxymethyl, unsubstituted or substituted with one R$_6$ substituent; heteroaryloxyethyl, unsubstituted or substituted with one R$_6$ substituent; heterocycloalkylbutyl, unsubstituted or substituted with one R$_6$ substituent;

R$_6$ is selected from the group consisting of fluorine and dialkylamino group.

Alternately, R$_1$ and R$_2$ together with the nitrogen atom to which they are attached may form an azacyclic ring selected from an azetidine, a pyrrolidine or a piperidine ring system.

Y$_1$ and Y$_2$ are independently selected from C or N;

R$_3$ and R$_4$ are independently selected from the group consisting of hydrogen, fluorine, and methyl.

According to a fourth embodiment of the invention, the compounds of Formula (I) can be selected from the group consisting of:

4-(4-fluorophenyl)-6-(methylamino)-3,4-dihydro-1,3,5-triazin-2(1H)-one;
6-(ethylamino)-4-(o-tolyl)-3,4-dihydro-1,3,5-triazin-2(1H)-one;
6-(ethylamino)-4-(4-fluorophenyl)-3,4-dihydro-1,3,5-triazin-2(1H)-one;
6-(ethylamino)-4-(4-fluorophenyl)-3,4-dihydro-1,3,5-triazin-2(1H)-one;
6-(ethylamino)-4-(4-fluorophenyl)-3,4-dihydro-1,3,5-triazin-2(1H)-one;
4-(4-fluorophenyl)-6-(propylamino)-3,4-dihydro-1,3,5-triazin-2(1H)-one;
4-(4-fluorophenyl)-6-(isopropylamino)-3,4-dihydro-1,3,5-triazin-2(1H)-one;
4-(4-fluorophenyl)-6-(isobutylamino)-3,4-dihydro-1,3,5-triazin-2(1H)-one;
4-(4-fluorophenyl)-6-(phenylamino)-3,4-dihydro-1,3,5-triazin-2(1H)-one;
6-(dimethylamino)-4-(4-fluorophenyl)-3,4-dihydro-1,3,5-triazin-2(1H)-one;
6-(diethylamino)-4-(4-fluorophenyl)-3,4-dihydro-1,3,5-triazin-2(1H)-one;
4-(4-fluorophenyl)-6-(piperidin-1-yl)-3,4-dihydro-1,3,5-triazin-2(1H)-one;
6-(butylamino)-4-(4-fluorophenyl)-3,4-dihydro-1,3,5-triazin-2(1H)-one;
6-(ethylamino)-4-(pyridin-3-yl)-3,4-dihydro-1,3,5-triazin-2(1H)-one;
4-(4-fluorophenyl)-6-(pyrrolidin-1-yl)-3,4-dihydro-1,3,5-triazin-2(1H)-one;
N-(4-(4-fluorophenyl)-6-oxo-1,4,5,6-tetrahydro-1,3,5-triazin-2-yl)acetamide;
N-(4-(4-fluorophenyl)-6-oxo-1,4,5,6-tetrahydro-1,3,5-triazin-2-yl)-2-propylpentanamide;
5-(1,2-dithiolan-3-yl)-N-(4-(4-fluorophenyl)-6-oxo-1,4,5,6-tetrahydro-1,3,5-triazin-2-yl)pentanamide;
3-((1H-benzo[d][1,2,3]triazol-1-yl)oxy)-N-(4-(4-fluorophenyl)-6-oxo-1,4,5,6-tetrahydro-1,3,5-triazin-2-yl)propanamide;
N-(4-(4-fluorophenyl)-6-oxo-1,4,5,6-tetrahydro-1,3,5-triazin-2-yl)-2-phenoxyacetamide;
2-(4-fluorophenoxy)-N-(4-(4-fluorophenyl)-6-oxo-1,4,5,6-tetrahydro-1,3,5-triazin-2-yl)acetamide;
6-((3-(dimethylamino)propyl)amino)-4-(4-fluorophenyl)-3,4-dihydro-1,3,5-triazin-2(1H)-one;
4-(4-fluorophenyl)-6-((3-(piperidin-1-yl)propyl)amino)-3,4-dihydro-1,3,5-triazin-2(1H)-one;
6-(benzylamino)-4-(4-fluorophenyl)-3,4-dihydro-1,3,5-triazin-2(1H)-one;
4-(4-fluorophenyl)-6-((pyridin-4-ylmethyl)amino)-3,4-dihydro-1,3,5-triazin-2(1H)-one;
6-(dipropylamino)-4-(4-fluorophenyl)-3,4-dihydro-1,3,5-triazin-2(1H)-one.

The following compounds may be synthesized with the same method used for the compounds above:

6-(cyclopropylamino)-4-(4-fluorophenyl)-3,4-dihydro-1,3,5-triazin-2(1H)-one;

6-((cyclopropylmethyl)amino)-4-(4-fluorophenyl)-3,4-dihydro-1,3,5-triazin-2(1H)-one;
6-((3-(diethylamino)propyl)amino)-4-(4-fluorophenyl)-3,4-dihydro-1,3,5-triazin-2(1H)-one;
4-(4-fluorophenyl)-6-((3-morpholinopropyl)amino)-3,4-dihydro-1,3,5-triazin-2(1H)-one;
4-(4-fluorophenyl)-6-((3-(4-methylpiperazin-1-yl)propyl)amino)-3,4-dihydro-1,3,5-triazin-2(1H)-one;
6-(azetidin-1-yl)-4-(4-fluorophenyl)-3,4-dihydro-1,3,5-triazin-2(1H)-one;
N-(4-(4-fluorophenyl)-6-oxo-1,4,5,6-tetrahydro-1,3,5-triazin-2-yl)propionamide;
  N-(4-(4-fluorophenyl)-6-oxo-1,4,5,6-tetrahydro-1,3,5-triazin-2-yl)butyramide;
  N-(4-(4-fluorophenyl)-6-oxo-1,4,5,6-tetrahydro-1,3,5-triazin-2-yl)isobutyramide;
  N-(4-(4-fluorophenyl)-6-oxo-1,4,5,6-tetrahydro-1,3,5-triazin-2-yl)-3-methylbutanamide.

The compounds exemplified in this invention may be prepared from readily available starting materials using the following general methods and procedures for example exemplified in Michael Smith, Jerry March—March's Advanced Organic Chemistry: reactions mechanisms and structure—6th Edition, John Wiley & Sons Inc., 2007.

It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W. Green and Peter G. M. Wuts—Protective Groups in Organic Synthesis, Fourth Edition, John Wiley & Sons Inc., 2006.

It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures.

The synthesis of a compound of Formula (I), according to the synthetic processes described below, can be conducted in a stepwise manner, whereby each intermediate is isolated and purified by standard purification techniques such as, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The compounds of Formula (I), prepared with the methods described herein below, may be treated or purified by conventional techniques or means for example by filtration, distillation, chromatography, recrystallization and combination thereof.

The salts of compounds of Formula (I) may be prepared by reacting a basic compound with the desired acid in solution.

General Procedures

In one embodiment, a compound of Formula (I) can be obtained by application of the chemical transformations reported in the schemes herein described.

Particularly, when $R_1$ is hydrogen, linear or branched $C_{1-6}$alkyl, $R_2$ is linear or branched unsubstituted or substituted $C_{1-6}$alkyl, $C_{2-6}$alkenyl, $C_{2-6}$alkynyl, unsubstituted or substituted $C_{3-6}$cycloalkyl or $C_{3-6}$cycloalkylC$_{1-6}$alkyl, unsubstituted or substituted aryl, heteroaryl, arylC$_{1-6}$alkyl, heteroarylC$_{1-6}$alkyl, heterocyclylC$_{1-6}$alkyl, or together with $R_1$ forms a $C_{4-7}$azacyclic ring including the nitrogen atom to which $R_1$ and $R_2$ are attached, and $R_3$, $R_4$, $Y_1$ and $Y_2$ are as defined above in Formula (I), the compounds of Formula (I) can be synthesized following Scheme 1.

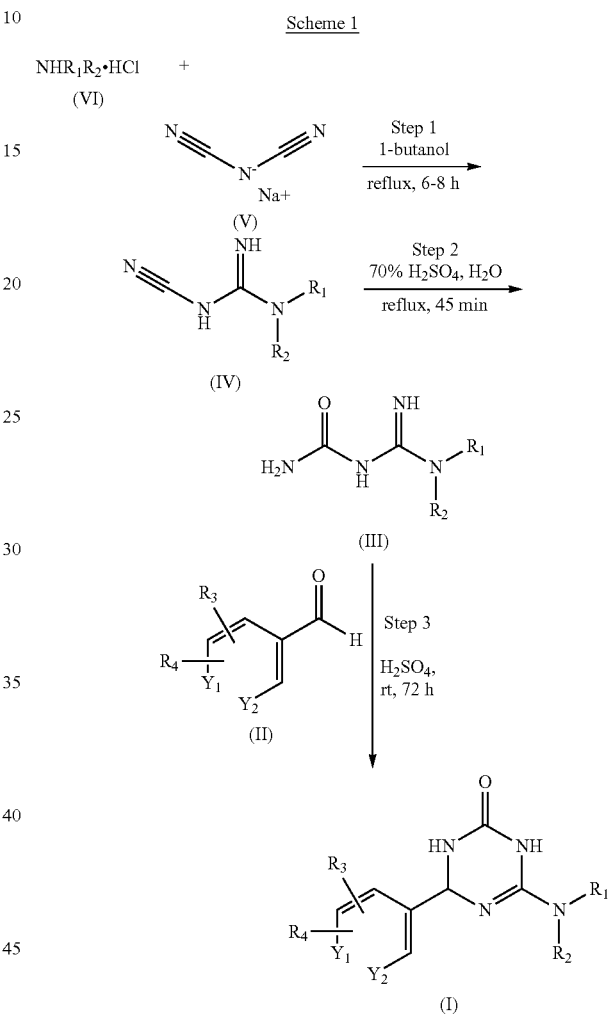

The compounds of Formula (I) can be prepared through a condensation reaction between commercially available benzaldehydes of Formula (II), wherein $R_3$, $R_4$, $Y_1$ and $Y_2$ are as defined above, and substituted guanylureas of Formula (III), wherein $R_1$ and $R_2$ are as defined above in Formula (I) [Ostrogovich, A., Gazzetta Chimica Italiana 1909, 39, 540-549].

As a general procedure, compounds of Formula (II) and (III) are dissolved in concentrated $H_2SO_4$ and the resulting reaction mixture is stirred at rt for 72 hours, affording the compounds of Formula (I) as racemates at the $C_4$ of the triazinone ring.

Guanylureas of Formula (III), as defined above, are either commercially available or can be prepared by acid-catalyzed hydration, heating at reflux for 45 minutes in 70% $H_2SO_4$, of cyanoguinidines of Formula (IV), wherein $R_1$ and $R_2$ are as defined above in Formula (I). Cyanoguanidines of Formula (IV) are either commercially available or can be prepared by heating at reflux for 6-8 hours in 1-butanol, the commercially available sodium dicyanoamide of Formula (V) with primary or secondary amines hydrochloride of Formula (VI), wherein $R_1$ and $R_2$ are as defined above in Formula (I).

Furthermore, when $R_1$ is hydrogen, linear or branched $C_{1-6}$alkyl, $R_2$ is $COR_5$ and $R_2$, $R_4$, $R_5$, $Y_1$ and $Y_2$ are as defined above in Formula (I), the compounds of Formula (I) can be synthesized following Scheme 2.

Scheme 2

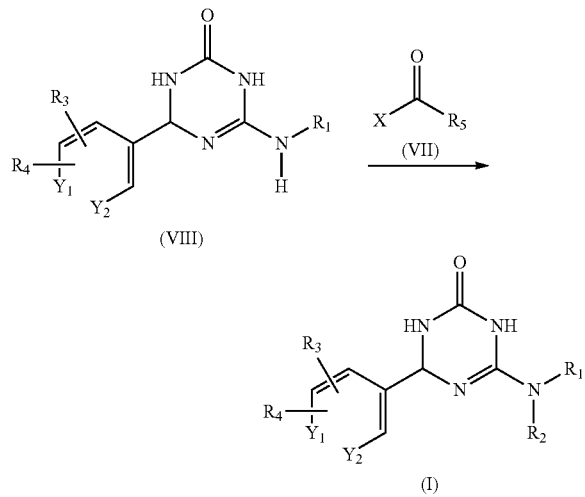

The compounds of Formula (I) can be prepared through a coupling reaction between acyl chlorides or carboxylic acids of Formula (VII), wherein X is a chlorine or and hydroxyl group, respectively, and $R_5$ is as defined in Formula (I), and intermediates of Formula (VIII), wherein and $R_1$, $R_3$, $R_4$, $Y_1$ and $Y_2$ are as defined above in Formula (I).

As a general procedure, when X is a chlorine, the coupling reaction is performed using a mixture of organic solvent, for example pyridine/DCM, DMF/DCM, 2,6-lutidine/DMF, stirring at rt for 3-4 hours.

When X is an hydroxyl group the coupling reaction is performed in DMF or DCM, in the presence of an activating agent such as EDCI.HCl or EDCI.HCl/HOBt and a base, preferably DIPEA or $Et_3N$, stirring overnight at rt.

Compounds of Formula (VIII), as defined above, can be synthesized according the procedure previously described in Scheme 1.

Single enantiomers of compounds of Formula (I) or compounds of Formula (VIII) can be obtained via separation by chiral HPLC.

A second aspect of the present invention is related to a pharmaceutical composition comprising a compound of Formula (I) as disclosed above and a pharmaceutically acceptable carrier, stabilizer, diluent or excipient thereof.

A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous and intravenous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, subcutaneous, intravenous, intramuscular, intranasal and pulmonary routes. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions.

Liquid forms suitable for oral administration may include a suitable aqueous or non-aqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable carriers known in the art.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring agent such as cherry or orange flavor. To prevent breakdown during transit through the upper portion of the gastrointestinal tract, the composition be an enteric coated formulation.

Compositions for pulmonary administration include, but are not limited to, dry powder compositions consisting of the powder of a compound of Formula (I) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I) per dosage unit for daily administration.

In some embodiments, the amounts effective for a specific formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

Concerning formulations with respect to any variety of routes of administration, methods and formulations for the administration of drugs are disclosed in Remington's Pharmaceutical Sciences, 17th Edition, Gennaro et al. Eds., Mack Publishing Co., 1985, and Remington's Pharmaceutical Sciences, Gennaro A R ed. 20th Edition, 2000, Williams & Wilkins Pa., USA, and Remington: The Science and Practice of Pharmacy, 21st Edition, Lippincott Williams & Wilkins Eds., 2005; and in Ansel's Pharmaceutical Dosage Forms and Drug Delivery Systems, 8th Edition, Lippincott Williams & Wilkins Eds., 2005.

The above described components for orally administered or injectable compositions are merely representative.

The compounds of this invention can also be administered in sustained release forms or from sustained release drug delivery systems.

Moreover, the pharmaceutical compositions according to the invention may comprise a second therapeutic agent, for example a neuroprotectant or a known agent for Alzheimer's disease treatment preferably selected from, but not limited to, (4aS,6R,8aS)-5,6,9,10,11,12-hexahydro-3-methoxy-11-methyl-4aH-[1]benzofuro[3a,3,2-ef][2]benzazepin-6-ol also known as galantamine, (S)-3-[1-(dimethylamino) ethyl]phenyl N-ethyl-N-methylcarbamate also known as rivastigmine, (RS)-2-[(1-benzyl-4-piperidyl)methyl]-5,6-dimethoxy-2,3-dihydroinden-1-one also known as donepezil, and 3,5-dimethyladamantan-1-amine also known as memantine.

A third aspect of the present invention is related to the use of compounds of Formula (I) as disclosed above or the pharmaceutical composition thereof, or their pharmaceutically acceptable salts or solvates as a medicament.

In fact, dual inhibitors of the BACE-1 and GSK-3β enzymes can find therapeutic exploitation in a large variety of pathological conditions of the central nervous system. In particular, these compounds can be utilized for the treatment or prevention of central nervous system diseases or disorders, more particularly cognitive, neurodegenerative or neuronal diseases or disorders. The disease or disorder is preferably selected from, but not limited to, chronic neurodegenerative conditions, including dementias such as Alzheimer's diseases, Parkinson's disease, panencephalitic parkinsonism, postencephalitic parkinsonism, Pick's disease, corticobasal degeneration, Huntington's disease, AIDS-related dementia, cancer-related dementia, type 2 diabetes-related cognitive impairment and type 2 diabetes-related dementia, amyotrophic lateral sclerosis, multiple sclerosis and neurotraumatic diseases selected from acute stroke and post stroke functional recovery, epilepsy, mood disorders selected from the group consisting of depression, schizophrenia and bipolar disorders, cerebral bleeding such as cerebral bleeding due to solitary cerebral amyloid angiopathy, motor neurone diseases, mild to severe cognitive impairment, ischaemia, head trauma, brain injury especially traumatic brain injury, Down's syndrome, Lewy body disease, inflammation and chronic inflammatory diseases.

In addition, these compounds can find application in the field of tauopathies, which are a class of neurodegenerative diseases associated with the pathological aggregation of the tau protein.

Hyperphosphorylation of tau can be responsible for the detachment of the protein from the neuronal microtubules, generating intracellular aggregates, also called neurofibrillary tangles (NFT). Alzheimer's disease per se is an example of tauopathie, being however the plethora of neurodegenerative diseases associated to the pathological aggregation of the tau protein much wider.

In particular, the present class of compounds can find application in the treatment of the following disorders: progressive supranuclear palsy; dementia pugilistica (chronic traumatic encephalopathy); frontotemporal dementia and parkinsonism linked to chromosome 17; Lytico-Bodig disease (Parkinson-dementia complex of Guam); tangle-predominant dementia, with NFTs similar to Alzheimer's, but without plaques; ganglioglioma and gangliocytoma; meningioangiomatosis; subacute sclerosing panencephalitis.

Furthermore, amyloidosis can also be treated with the compounds of the present invention in light of their ability to reduce the formation of amyloid plaques.

Amyloidosis refers to a variety of conditions wherein normally soluble proteins become insoluble and are deposited in the extracellular space of various organs or tissues, disrupting normal function. Among these pathological conditions, the following illnesses can be treated with the compounds of the invention: senile systemic amyloidosis; prion protein related diseases, including the Creutzfeldt-Jakob disease; cerebral amyloid angiopathy; familial corneal amyloidosis, hereditary cerebral hemorrhage with amyloidosis of the Dutch-Type.

In particular, compounds of Formula (I) can be used in the treatment or prevention of a disease or disorder selected from the group consisting of Alzheimer's diseases, Parkinson's disease, Huntington's disease, amyotrophic lateral sclerosis, multiple sclerosis, neurotraumatic diseases such as acute stroke and post stroke functional recovery, epilepsy, mood disorders selected from the group consisting of depression, schizophrenia and bipolar disorders, cerebral bleeding, ischaemia, mild to severe cognitive impairment, head trauma, brain injury especially traumatic brain injury, inflammation and chronic inflammatory diseases, dementias selected from the group consisting of AIDS-related dementia, cancer-related dementia, type 2 diabetes-related dementia, dementia pugilistica, frontotemporal dementia, Parkinson-dementia complex of Guam, tangle-predominant dementia.

In the following, the present invention shall be illustrated by means of some examples, which are not construed to be viewed as limiting the scope of the invention.

The following abbreviations are hereinafter used in the accompanying examples: acetic acid (AcOH), acetonitrile (MeCN), acetyl chloride (AcCl), ammonia ($NH_3$), ammonium acetate ($NH_4OAc$), deuterated chloroform ($CDCl_3$), deuterated dimethylsulfoxide (DMSO-$d_6$), deuterated methanol ($CD_3OD$), deuterium oxide ($D_2O$), dichloromethane (DCM), diethyl ether ($Et_2O$), N,N-diisopropylethylamine (DIPEA), 1-(3-dimethylaminopropyl)-3-ethylcarbodiimide hydrochloride (EDCI.HCl), dimethylformamide (DMF), dimethylsulfoxide (DMSO), ethanol (EtOH), ethyl acetate (EtOAc), hydrochloric acid (HCl), hydroxybenzotriazole hydrate (HOBt), lithium chloride (LiCl), methanol (MeOH), room temperature (rt), sodium carbonate ($Na_2CO_3$), sodium hydroxide (NaOH), sodium sulphate ($Na_2SO_4$), sulfuric acid ($H_2SO_4$), triethylamine ($Et_3N$), trifluoroacetic acid (TFA), water ($H_2O$).

Chemicals, Materials and Methods

All the commercial available reagents and solvents were used as purchased from Sigma-Aldrich, Fluka (Italy), without further purification.

Column chromatography purifications were performed under flash conditions using Sigma Aldrich silica gel grade 9385, 60 Å, 230-400 mesh. Thin layer chromatography (TLC) were performed on 0.20 mm silica gel 60 F254 plates (Merck, Germany), which were visualized by exposure to ultraviolet light (254 and 366 nm), and potassium permanganate stain. Reactions involving generation or consumption of amine were visualized by using bromocresol green spray (0.04% in EtOH made blue by NaOH) following heating of the plate. Compounds were named following IUPAC rules as applied by ChemBioDraw Ultra (version 13.0).

Nuclear magnetic resonance (NMR) experiments were run on Varian VXR 200 or Bruker Avance III 400 (200 or 400 MHz for $^1H$; 50 or 100 MHz for $^{13}C$). Spectra were acquired at 300 K, using DMSO-$d_6$, $CD_3OD$, $D_2O$ or $CDCl_3$ as solvents. Chemical shifts for $^1H$ and $^{13}C$ spectra were recorded in parts per million (ppm) using the residual non-deuterated solvent as the internal standard. Data are reported as follows: chemical shift (ppm), multiplicity (indicated as: s, singlet; br s, broad singlet; exch, exchangeable proton with $D_2O$; d, doublet; t, triplet; q, quartet; m, multiplet and combinations thereof), coupling constants (J) in Hertz (Hz) and integrated intensity.

UPLC-MS analyses were run on a Waters ACQUITY UPLC-MS system consisting of a SQD (single quadrupole detector) mass spectrometer (MS) equipped with an electrospray ionization (ESI) interface and a photodiode array detector (PDA). PDA range was 210-400 nm. Analyses were performed on an ACQUITY UPLC HSS T3 $C_{18}$ column (50 mm×2.1 mm i.d., particle size 1.8 µm) with a VanGuard HSS T3 $C_{18}$ pre-column (5 mm×2.1 mm i.d., particle size 1.8 µm). Mobile phase was either 10 mM $NH_4OAc$ in $H_2O$ at pH 5 adjusted with AcOH (A) and 10 mM $NH_4OAc$ in MeCN—$H_2O$ (95:5) at pH 5 (B). ESI in positive and negative modes was applied, in the mass scan range 100-500 Da.

Analyses by chiral HPLC were run on a Waters Alliance HPLC instrument consisting of an e2695 separation module and a 2998 PDA. PDA range was 210-400 nm. Analyses were performed isocratic on a Daicel ChiralPak AD column (250 mm×4.6 mm i.d., particle size 10 µm). Mobile phase was 0.1% TFA Heptane/EtOH (90:10). Separations by preparative chiral HPLC were run on a Waters Alliance HPLC instrument consisting of a 1525 binary HPLC pump, waters fraction collector III and a 2998 PDA. UV detection was at 215 nm. Purifications were performed isocratic on a Daicel ChiralPak AD column (250 mm×10 mm i.d., particle size 10 µm). Mobile phase was 0.1% TFA Heptane/EtOH (90:10).

Optical rotations were measured on a Rudolf Research Analytical Autopol II automatic polarimeter using a sodium lamp (589 nm) as the light source; concentrations expressed in g/100 mL using MeOH as a solvent and a 1 dm cell.

All the finals compounds showed ≥95% purity by NMR and UPLC-MS analysis.

With the aim of better illustrating the present invention, the syntheses of example compounds reported in the FIG. 1 are provided.

The compounds reported in FIG. 1 were synthesized as described below.

PREPARATIONS AND EXAMPLES

Preparation I (Examples 1-15, 22-26)

General synthesis of compounds of Formula (I) wherein $R_1$ is hydrogen, linear or branched unsubstituted or substituted $C_{1-6}$alkyl, $R_2$ is linear or branched unsubstituted or substituted $C_{1-6}$alkyl, unsubstituted or substituted aryl, unsubstituted or substituted heteroaryl, unsubstituted or substituted aryl$C_{1-6}$alkyl, unsubstituted or substituted heteroaryl$C_{1-6}$alkyl, unsubstituted or substituted heterocyclyl$C_{1-6}$alkyl, or $R_1$ and $R_2$ together with the nitrogen atom to which they are attached may form a 4 to 7 membered azacyclic ring containing up to three heteroatoms selected from nitrogen and oxygen, and $R_3$, $R_4$, $Y_1$ and $Y_2$ are as defined in Formula (I).

General Procedure (A): Synthesis of Intermediates of Formula (IV)—Step 1, Scheme 1

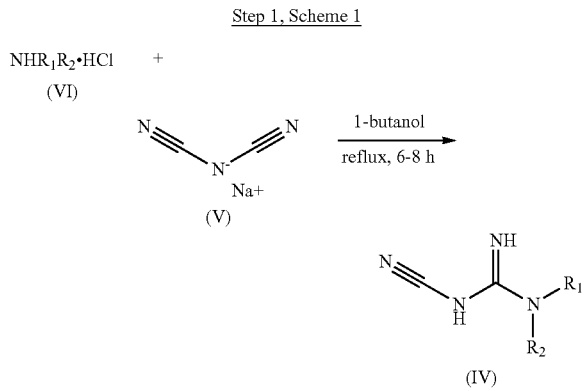

To a suspension of sodium dicyanamide (V) (1.2 eq.) in 1-butanol (1.2 M), was added the proper amine hydrochloride (VI) (1.0 eq.). The resulting mixture was heated at reflux for 6-8 hours, affording a white precipitate, which was filtered off. The filtrate was concentrated under vacuum to yield crude cyanoguinidine (IV). Further purification by flash chromatography was performed when required.

(IVa) N-cyano-N'-methylguanidine

The title compound was obtained according to general procedure A using methylamine hydrochloride (0.63 g, 9.30 mmol). The crude material was triturated with $Et_2O$, affording IVa as a yellow oil, which was used in the next step without further purification: 0.72 g (77%). $^1$H-NMR ($CD_3OD$, 400 MHz) δ 2.74 (s, 3H). $^{13}$C-NMR ($CD_3OD$, 100 MHz) δ 28.4, 120.2, 163.4.

(IVb) N-cyano-N'-ethylguanidine

The title compound was obtained according to general procedure A using ethylamine hydrochloride (2.29 g, 27.07 mmol). Elution with DCM/MeOH/33% aqueous $NH_3$ solution (9:1:0.1) afforded IVb as a yellow oil: 2.5 g (73%). $^1$H-NMR ($D_2O$, 400 MHz) δ 1.19 (t, J=6.8, 3H), 3.23 (q, J=6.8, 2H). $^{13}$C-NMR ($D_2O$, 100 MHz) δ 13.3, 36.5, 120.5, 161.1.

(IVc) N-cyano-N'-propylguanidine

The title compound was obtained according to general procedure A using propylamine hydrochloride (2.30 g, 24.53 mmol). Elution with DCM/MeOH/33% aqueous $NH_3$ solution (9:1:0.1) afforded IVc as a waxy solid: 1.9 g (63%). $^1$H-NMR ($CD_3OD$, 400 MHz) δ 0.90 (t, J=7.2, 3H), 1.49-1.54 (m, 2H), 3.09 (t, J=6.8, 2H). $^{13}$C-NMR ($CD_3OD$, 100 MHz) δ 10.1, 22.2, 42.8, 118.8, 161.7.

(IVd) N-cyano-N'-isopropylguanidine

The title compound was obtained according to general procedure A using isopropylamine hydrochloride (0.89 g, 9.30 mmol). The crude material was triturated with $Et_2O$ and DCM, affording IVd as a white solid, which was used in the next step without further purification: 0.80 g (69%). $^1$H-NMR ($CD_3OD$, 400 MHz) (4.5:1 mixture of rotamers) δ 1.12 (d, J=6.0, 1.1H, $2CH_3$ minor), 1.29 (d, J=6.0, 4.9H, $2CH_3$ major), 3.37-3.43 (m, 0.8H, CH major), 3.52-3.58 (m, 0.2, CH minor). $^{13}$C-NMR ($CD_3OD$, 100 MHz) δ 19.6 ($2CH_3$ major), 21.6 ($2CH_3$ minor), 43.3 (CH minor), 43.9 (CH major), 119.1, 165.3.

(IVe) N-cyano-N'-isobutylguanidine

The title compound was obtained according to general procedure A using isobutylamine hydrochloride (1.02 g, 9.30 mmol). The crude material was triturated with $Et_2O$ and DCM, affording IVe as a woxy solid, which was used in the next step without further purification: 1.23 g (95%). $^1$H-NMR ($CD_3OD$, 400 MHz) δ 0.88 (d, J=6.8, 6H), 1.75-1.78 (m, 1H), 2.95 (d, J=7.2, 2H). $^{13}$C-NMR ($CD_3OD$, 100 MHz) δ 19.0, 28.2, 48.4, 119.1, 161.7.

(IVf) N-cyano-N'-phenylguanidine

The title compound was obtained according to general procedure A using aniline hydrochloride (0.65 g, 5.05 mmol). The crude material was triturated with $H_2O$, affording IVf as a white solid, which was used in the next step without further purification: 0.80 g (quantitative yield). $^1$H-NMR (DMSO-$d_6$, 400 MHz) δ 6.98 (br s, exch, 2H), 7.05-7.09 (m, 1H), 7.28-7.35 (m, 2H), 9.03 (br s, exch, 1H). $^{13}$C-NMR (DMSO-$d_6$, 100 MHz) δ 117.6, 121.7, 124.2, 129.2, 138.4, 159.9.

(IVg) N-cyano-N',N'-dimethylguanidine

The title compound was obtained according to general procedure A using dimethylamine hydrochloride (1.52 g, 18.72 mmol). The crude material was triturated with DCM, affording IVg as a white solid, which was used in the next step without further purification: 0.40 g (18%). $^1$H-NMR ($CD_3OD$, 400 MHz) δ 2.77 (s, 6H). $^{13}$C-NMR ($CD_3OD$, 100 MHz) δ 36.5, 119.0, 161.1.

(IVh) N-cyano-N',N'-diethylguanidine

The title compound was obtained according to general procedure A using diethylamine hydrochloride (1.02 g, 9.30 mmol). The crude material was triturated with $Et_2O$, affording IVh as a yellow solid, which was used in the next step without further purification: 0.95 g (73%). $^1$H-NMR ($CD_3OD$, 400 MHz) (1.5:1 mixture of rotamers) δ 1.13 (t, J=6.8, 3.6H, $2CH_3$ major), 1.30 (t, J=6.8, 2.4H, $2CH_3$ minor), 3.04 (q, J=6.8, 1.8H, $2CH_2$ minor), 3.5 (q, J=6.8, 2.2H, $2CH_2$ major). $^{13}$C-NMR ($CD_3OD$, 100 MHz) δ 10.3 ($2CH_3$ minor), 12.0 ($2CH_3$ major), 42.2 ($2CH_2$ minor), 42.5 ($2CH_2$ major), 119.3, 159.8.

(IVi) N-cyano-1-piperidinecarboximidamide

The title compound was obtained according to general procedure A using piperidine hydrochloride (1.13 g, 9.30 mmol). The crude material was triturated with DCM, affording IVi as a white solid, which was used in the next step without further purification: 0.46 g (33%). $^1$H-NMR ($CD_3OD$, 400 MHz) δ 1.52-1.57 (m, 4H), 1.62-1.67 (m, 2H), 3.44-3.46 (m, 4H). $^{13}$C-NMR ($CD_3OD$, 100 MHz) δ 23.7, 25.2, 45.7, 119.2, 159.9.

(IVj) N-cyano-N'-butylguanidine

The title compound was obtained according to general procedure A using butylamine hydrochloride (1.02 g, 9.30 mmol). The crude material was triturated with DCM, affording IVj as a gummy solid, which was used in the next step without further purification: 1.12 g (86%). $^1$H-NMR (DMSO-$d_6$, 400 MHz) δ 0.83-0.88 (m, 3H), 1.22-1.27 (m, 2H), 1.29-1.39 (m, 2H), 3.00-3.02 (m, 2H). $^{13}$C-NMR (DMSO-$d_6$, 100 MHz) δ 14.0, 19.8, 31.5, 40.11, 118.8, 161.6.

(IVk) N-cyano-1-pyrrolidinecarboximidamide

The title compound was obtained according to general procedure A using pyrrolidine hydrochloride (1.00 g, 9.30 mmol). The crude material was triturated with $Et_2O$, affording IVk as a light yellow solid, which was used in the next step without further purification: 0.97 g (76%). $^1$H-NMR (DMSO-$d_6$, 400 MHz) δ 1.76-1.78 (m, 4H), 3.20-3.23 (m, 4H). $^{13}$C-NMR (DMSO-$d_6$, 100 MHz) δ 25.3, 47.2, 118.8, 159.0.

(IVl) N-cyano-N'-(dimethylpropan-3-amino)guanidine

The title compound was obtained according to general procedure A using $N^1,N^1$-dimethylpropane-1,3-diamine dihydrochloride (0.51 g, 2.90 mmol). The crude material was taken up with 40 mL of MeOH/2N aqueous HCl solution (1:0.5), split in two parts, loaded onto two 2 g ISOLUTE SCX-2 columns, and eluted with MeOH/33% aqueous NH₃ solution (1:0.1) (2×15 mL). The organic phase was concentrated under vacuum, affording Ivl as a gummy solid, which was used in the next step without further purification: 0.10 g (21%). $^1$H-NMR (CD₃OD, 400 MHz) δ 1.68-1.76 (m, 2H), 2.24 (s, 6H), 2.33-2.39 (m, 2H), 3.16-3.22 (m, 2H). $^{13}$C-NMR (CD₃OD, 100 MHz) δ 26.8, 38.4, 44.0, 56.1, 118.7, 160.1.

(IVm) N-cyano-N'-(3-(piperidin-1-yl)propan)guanidine

The title compound was obtained according to general procedure A using 3-(piperidin-1-yl)propan-1-amine dihydrochloride (0.51 g, 2.36 mmol). The crude material was taken up with 20 mL of saturated aqueous Na₂CO₃ solution and extracted with EtOAc (3×20 mL). The organic layers were collected, dried over anhydrous Na₂SO₄, filtered and evaporated under vacuum. The residue was purified with flash chromatography, eluting with DCM/MeOH/33% aqueous NH₃ solution (8:2:0.2). IVm was obtained as a gummy solid: 0.34 g (45%). $^1$H-NMR (CD₃OD, 400 MHz) δ 1.44-1.48 (m, 2H), 1.59-1.65 (m, 4H), 1.70-1.77 (m, 2H), 2.44-2.56 (m, 6H), 3.17 (t, J=6.4, 2H). $^{13}$C-NMR (CD₃OD, 100 MHz) δ 23.4, 24.7, 25.5, 39.2, 53.8, 55.5, 118.7, 161.8.

(IVn) N-cyano-N'-benzylguanidine

The title compound was obtained according to general procedure A using benzylamine hydrochloride (1.34 g, 9.36 mmol). Elution with DCM/MeOH/33% aqueous NH₃ solution (9:1:0.1) afforded IVn as a gummy solid: 0.81 g (50%). $^1$H-NMR (CD₃OD, 400 MHz) 4.30 (s, 2H), 7.18-7.29 (m, 5H). $^{13}$C-NMR (CD₃OD, 100 MHz) δ 44.7, 119.0, 127.0, 127.2, 128.4, 138.1, 161.7.

(IVo) N-cyano-N'-pyridin-4-ylmethylguanidine

The title compound was obtained according to general procedure A using pyridin-4-ylmethanamine dihydrochloride (1.69 g, 9.36 mmol). Elution with DCM/MeOH/33% aqueous NH₃ solution (8:2:0.2) afforded IVo as a gummy solid: 0.93 g (57%). $^1$H-NMR (CD₃OD, 400 MHz) 4.40 (s, 2H), 7.25 (d, J=5.6, 2H), 8.39 (d, J=5.6, 2H). $^{13}$C-NMR (CD₃OD, 100 MHz) δ 43.4, 118.7, 122.2, 147.6, 148.8, 161.9.

(IVp) N-cyano-N',N'-dipropylguanidine

The title compound was obtained according to general procedure A using dipropylamine hydrochloride (0.94 g, 9.30 mmol). The crude material was taken up with EtOAc and washed with water. The organic layer was concentrated under vacuum, affording IVp as a colourless oil, which was used in the next step without further purification: 0.76 g (50%). $^1$H-NMR (CD₃OD, 400 MHz) δ 0.88 (t, J=7.2, 6 H), 1.55-1.60 (m, 4H), 3.24 (t, J=7.6, 4H). $^{13}$C-NMR (CD₃OD, 100 MHz) δ 10.2, 20.6, 49.8, 119.4, 160.3.

General Procedure (B): Synthesis of Intermediates of Formula (III)—Step 2, Scheme 1

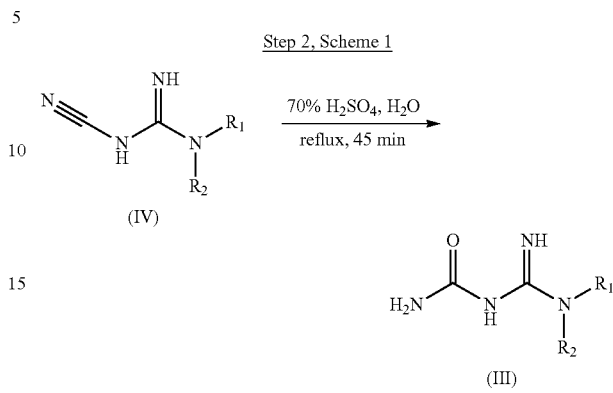

To a solution of cyanoguanidine (IV) (1 eq.) in water (1.2 M) was added 70% aqueous sulfuric acid (2 eq.). The resulting mixture was stirred at rt for 15 minutes and heated at reflux for 1 hours. The reaction mixture was then cooled to rt and basified with Na₂CO₃. The aqueous phase was evaporated in vacuo, and the crude material was taken up with MeOH. The residue was filtered off and the organic solvent was concentrated under vacuum, to afford compound III, which was used in the next step without further purification.

(IIIa) (N'-methylcarbamimidoyl)urea

The title compound was obtained according to general procedure B using IVa (0.77 g, 7.12 mmol). IIIa was obtained as a yellow oil: 0.66 g (83%). $^1$H-NMR (CD₃OD, 200 MHz) δ 2.80 (s, 3H). $^{13}$C-NMR (CD₃OD, 50 MHz) δ 26.1, 161.2, 166.9.

(IIIb) (N'-ethylcarbamimidoyl)urea

The title compound was obtained according to general procedure B using IVb (2.50 g, 20.46 mmol). IIIb was obtained as a gummy solid: 3.90 g (quantitative yield). $^1$H-NMR (D₂O, 400 MHz) δ 0.48 (t, J=6.8, 3H), 2.58 (q, J=6.8, 2H). $^{13}$C-NMR (D₂O, 100 MHz) δ 12.1, 35.8, 152.8, 155.2.

(IIIc) (N'-propylcarbamimidoyl)urea

The title compound was obtained according to general procedure B using IVc (1.80 g, 14.26 mmol). IIIc was obtained as a gummy solid: 2.40 g (quantitative yield). $^1$H-NMR (D₂O, 400 MHz) δ 0.49-0.54 (m, 3H), 1.14-1.25 (m, 2H), 2.71 (t, J=6.8, 1H), 2.83 (t, J=6.8, 1H). $^{13}$C-NMR (D₂O, 100 MHz) δ 10.1, 21.1, 42.6, 155.7, 156.3.

(IIId) (N'-isopropylcarbamimidoyl)urea

The title compound was obtained according to general procedure B using IVd (0.80 g, 6.39 mmol). IIId was obtained as a gummy solid: 0.50 g (54%). $^1$H-NMR (CD₃OD, 400 MHz) (1.1:1 mixture of rotamers) δ 1.25 (d, J=6.8, 3.1H, 2CH₃ major), 1.29 (d, J=6.8, 2.9H, 2CH₃ minor), 3.39-3.46 (m, 0.48H, CH minor), 3.81-3.88 (m, 0.52H, CH major). $^{13}$C-NMR (CD$_3$OD, 100 MHz) δ 19.6 (2CH$_3$ major), 21.0 (2CH$_3$ minor), 43.9 (CH major), 44.0 (CH minor), 153.3, 155.6.

(IIIe) (N'-isobutylcarbamimidoyl)urea

The title compound was obtained according to general procedure B using IVe (1.23 g, 8.77 mmol). IIIe was obtained as a gummy solid: 1.39 g (quantitative yield). $^1$H-NMR (CD$_3$OD, 400 MHz) (2.3:1 mixture of rotamers) δ 0.23 (d, J=5.2, 4.2H, 2CH$_3$ major), 0.42 (d, J=5.2, 1.8H, 2CH$_3$ minor), 0.51-0.53 (m, 0.3H, CH minor), 1.16-1.18 (m, 0.7H, CH major), 2.39 (d, J=6.8, 0.6H, CH$_2$ minor) 2.87 (d, J=6.8, 1.4H, CH$_2$ major). $^{13}$C-NMR (CD$_3$OD, 100 MHz) δ 16.2 (2CH$_3$ minor), 18.0 (2CH$_3$ major), 26.7 (CH major+minor), 47.4 (CH$_2$ minor), 47.5 (CH$_2$ major) 153.6, 154.6.

(IIIf) (N'-phenylcarbamimidoyl)urea

The title compound was obtained according to general procedure B using IVf (0.80 g, 4.90 mmol). IIIf was obtained as a white solid: 0.72 g (82%). $^1$H-NMR (CDCl$_3$, 400 MHz) δ 7.01-7.06 (m, 3H), 7.21-7.25 (m, 2H). $^{13}$C-NMR (CDCl$_3$, 100 MHz) δ 124.0, 125.0, 129.5, 140.0, 155.6, 163.6.

(IIIg) (N',N'-dimethylcarbamimidoyl)urea

The title compound was obtained according to general procedure B using IVg (0.72 g, 5.89 mmol). IIIg was obtained as a white solid: 0.46 g (60%). $^1$H-NMR (DMSO, 400 MHz) δ 2.86 (s, 6H). $^{13}$C-NMR (DMSO, 100 MHz) δ 36.5, 160.8, 167.0.

(IIIh) (N',N'-dimethylcarbamimidoyl)urea

The title compound was obtained according to general procedure B using IVh (0.95 g, 6.76 mmol). IIIh was obtained as a yellow oil: 0.73 g (68%). $^1$H-NMR (CD$_3$OD, 400 MHz) (4.2:1 mixture of rotamers) δ 1.11 (t, J=6.8, 4.8H, 2CH$_3$ major), 1.18 (t, J=6.8, 1.2H, 2CH$_3$ minor), 3.36 (q, J=6.8, 3.2H, 2CH$_2$ major), 3.46 (q, J=6.8, 0.8H, 2CH$_2$ major). $^{13}$C-NMR (CD$_3$OD, 100 MHz) δ 12.0 (2CH$_3$ minor), 12.6 (2CH$_3$ major), 41.4 (2CH$_2$ major), 43.1 (2CH$_2$ minor), 158.9, 167.1.

(IIIi) (piperidine-1-carboximidoyl)urea

The title compound was obtained according to general procedure B using IVi (0.46 g, 3.02 mmol). IIIi was obtained as a gummy solid: 0.51 g (quantitative yield). $^1$H-NMR (CD$_3$OD, 400 MHz) δ 1.65-1.73 (m, 6H), 3.50-3.59 (m, 4H). $^{13}$C-NMR (CD$_3$OD, 100 MHz) δ 23.1, 24.9, 46.9, 153.2, 155.3.

(IIIj) (N'-butylcarbamimidoyl)urea

The title compound was obtained according to general procedure B using IVj (1.07 g, 7.64 mmol). IIIj was obtained as a gummy solid: 1.15 g (95%). $^1$H-NMR (DMSO-d$_6$, 400 MHz) δ 0.85-0.89 (m, 3H), 1.27-1.33 (m, 2H), 1.36-1.43 (m, 2H), 3.04-3.08 (m, 2H). $^{13}$C-NMR (DMSO-d$_6$, 100 MHz) δ 13.7, 19.5, 31.3, 39.6, 160.3, 166.8.

(IIIk) (pyrrolidine-1-carboximidoyl)urea

The title compound was obtained according to general procedure B using IVk (0.97 g, 7.04 mmol). IIIk was obtained as a light yellow solid: 0.80 g (73%). $^1$H-NMR (DMSO-d$_6$, 400 MHz) δ 1.76-1.79 (m, 4H), 3.25-3.28 (m, 4H). $^{13}$C-NMR (DMSO-d$_6$, 100 MHz) δ 25.1, 46.2, 155.9, 158.1.

(IIIl) (N'-(dimethylpropan-3-amino)carbamimidoyl) urea

The title compound was obtained according to general procedure B using IVl (0.10 g, 0.61 mmol). IIIl was obtained as a yellow gummy solid: 0.11 g (95%). $^1$H-NMR (CD$_3$OD, 400 MHz) δ 1.71-1.76 (m, 2H), 2.25 (s, 6H), 2.37 (t, J=7.6, 2H), 3.20 (t, J=7.6, 2H). $^{13}$C-NMR (CD$_3$OD, 100 MHz) δ 26.7, 38.3, 43.9, 56.3, 155.3, 156.4.

(IIIm) (N'-(3-(piperidin-1-yl)propan))carbamimidoyl) urea

The title compound was obtained according to general procedure B using IVm (0.34 g, 1.62 mmol). IIIm was obtained as a yellow gummy solid: 0.23 g (93%). $^1$H-NMR (CD$_3$OD, 400 MHz) δ 1.42-1.48 (m, 2H), 1.59-1.63 (m, 4H), 1.76-1.83 (m, 2H), 2.48-2.52 (m, 6H), 3.24-3.31 (m, 2H). $^{13}$C-NMR (CD$_3$OD, 100 MHz) δ 23.6, 24.9, 25.3, 38.7, 53.7, 54.8, 157.4, 159.5.

(IIIn) (N'-benzylcarbamimidoyl)urea

The title compound was obtained according to general procedure B using IVn (0.80 g, 4.60 mmol). IIIn was obtained as a white solid: 0.82 g (93%). $^1$H-NMR (CD$_3$OD, 400 MHz) δ 4.35 (s, 2H), 7.21-7.30 (m, 5H). $^{13}$C-NMR (CD$_3$OD, 100 MHz) δ 44.1, 126.9, 127.0, 128.1, 128.3, 160.9, 167.5.

(IIIo) (N'-pyridin-4-ylmethylcarbamimidoyl)urea

The title compound was obtained according to general procedure B using IVo (0.93 g, 5.31 mmol). IIIo was obtained as a gummy solid: 0.86 g (85%). $^1$H-NMR (CD$_3$OD, 400 MHz) δ 4.49 (s, 2H), 7.34 (d, J=5.6, 2H), 8.44 (d, J=5.6, 2H). $^{13}$C-NMR (CD$_3$OD, 100 MHz) δ 42.7, 122.2, 147.6, 148.7, 159.8, 165.6.

(IIIp) (N',N'-dipropylcarbamimidoyl)urea

The title compound was obtained according to general procedure B using IVp (0.77 g, 4.60 mmol). IIIp was obtained as a white solid: 0.68 g (79%). $^1$H-NMR (CD$_3$OD, 400 MHz) δ 0.79 (t, J=7.2, 6H), 1.42-1.48 (m, 4H), 3.16 (t, J=7.6, 4H). $^{13}$C-NMR (CD$_3$OD, 100 MHz) δ 11.5, 21.2, 48.2, 159.7, 167.2.

General Procedure (C): Synthesis of Compounds of Formula (I)—Step 3, Scheme 1

Step 3, Scheme 1

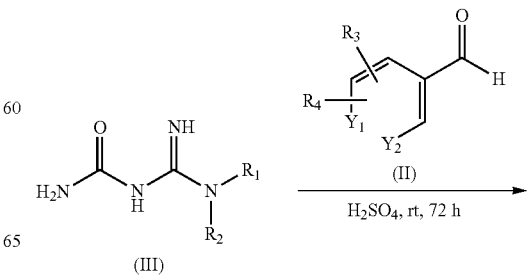

-continued

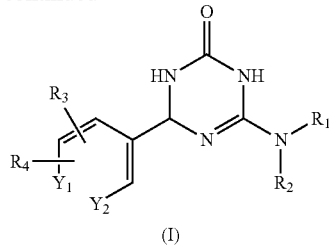

To a solution of guanylurea (III) (1 eq) in concentrated $H_2SO_4$ (5.5 M) was added the proper benzaldehyde (II) (1.2 eq). After stirring at rt for 72 hours, the reaction mixture was diluted with a small amount of cold $H_2O$. The solution was then made basic with $Na_2CO_3$, affording a precipitate which was collected by filtration. Whereas no precipitation was observed, the aqueous phase was concentrated in vacuo. The crude triazinone (I) was either purified by trituration with organic solvents or by flash chromatography.

Example 1

4-(4-fluorophenyl)-6-(methylamino)-3,4-dihydro-1,3,5-triazin-2(1H)-one

The title compound was obtained according to general procedure C using 4-fluoro-benzaldheyde (IIa) (0.73 mL, 6.84 mmol) and IIIa (0.66 g, 5.7 mmol). Elution with DCM/MeOH/33% aqueous $NH_3$ solution (8.5:1.5:0.1) afforded the compound of example 1 as a white solid: 0.33 g (26%). $^1$H-NMR ($CD_3OD$, 400 MHz) δ 2.76 (s, 3H), 5.68 (s, 1H), 7.07-7.12 (m, 2H), 7.42-7.45 (m, 2H). $^{13}$C-NMR ($CD_3OD$, 100 MHz) δ 26.5, 66.0, 115.0 (d, J=16.0), 128.1 (d, J=8.3), 138.1, 150.7, 154.2, 162.9 (d, J=244). MS (ESI) m/z: 223 [M+H]$^+$; MS (ESI) m/z: 221 [M−H]$^-$.

Example 2

6-(ethylamino)-4-(o-tolyl)-3,4-dihydro-1,3,5-triazin-2(1H)-one

The title compound was obtained according to general procedure C using o-tolyl-benzaldheyde-benzaldheyde (IIb) (0.36 mL, 3.19 mmol) and IIIb (0.34 g, 2.65 mmol). Elution with DCM/MeOH/33% aqueous $NH_3$ solution (9:1:0.1) afforded the compound of example 2 as a white solid: 0.26 g (43%). $^1$H-NMR (DMSO-$d_6$, 400 MHz) δ 1.02 (t, J=8.0, 3H), 2.37 (s, 3H), 3.05 (q, J=8.0, 2H), 5.32 (br s, exch, 1H), 5.77 (s, 1H), 7.14-7.16 (m, 3H), 7.25-7.27 (m, 1H), 7.35 (br s, exch, 1H), 8.48 (br s, exch, 1H). $^{13}$C-NMR (DMSO-$d_6$, 100 MHz) δ 15.4, 19.1, 35.3, 67.1, 126.4, 126.6, 130.7, 131.3, 135.7, 141.9, 148.3, 153.5. MS (ESI) m/z: 233 [M+H]$^+$.

Example 3

6-(ethylamino)-4-(4-fluorophenyl)-3,4-dihydro-1,3,5-triazin-2(1H)-one

The title compound was obtained according to general procedure C using 4-fluoro-benzaldheyde (IIa) (0.50 mL, 4.60 mmol) and IIIb (0.50 g, 3.84 mmol). Trituration with a mixture of organic solvents (DCM/MeOH) afforded the compound of example 3 as a white solid: 0.46 g (50%). $^1$H-NMR ($CD_3OD$, 400 MHz) δ 1.11 (t, J=8.0, 3H), 3.20 (q, J=8.0, 2H), 5.65 (s, 1H), 7.06-7.10 (m, 2H), 7.40-7.43 (m, 2H). $^{13}$C-NMR ($CD_3OD$, 100 MHz) δ 14.9, 36.7, 67.5, 116.3 (d, J=22.0), 129.5 (d, J=8.0), 139.6, 156.6, 158.5, 164.2 (d, J=244.0). MS (ESI) m/z: 237 [M+H]$^+$; MS (ESI) m/z: 235 [M−H]$^-$.

Example 4

(+)6-(ethylamino)-4-(4-fluorophenyl)-3,4-dihydro-1,3,5-triazin-2(1H)-one

The title compound was obtained, as a white solid, by chiral HPLC enantiomeric separation of the racemic compound of Example 3: 0.046 g (61%). ee>99.5% (detector UV 240 nm). Retention time on analytical chiral HPLC: 8.475 min. $^1$H-NMR ($CD_3OD$, 400 MHz) δ 1.11 (t, J=8.0, 3H), 3.20 (q, J=8.0, 2H), 5.65 (s, 1H), 7.06-7.10 (m, 2H), 7.40-7.43 (m, 2H). $^{13}$C-NMR ($CD_3OD$, 100 MHz) δ 14.9, 36.7, 67.5, 116.3 (d, J=22.0), 129.5 (d, J=8.0), 139.6, 156.6, 158.5, 164.2 (d, J=244.0). MS (ESI) m/z: 237 [M+H]$^+$; MS (ESI) m/z: 235 [M−H]$^-$. $[\alpha]^{20}_D$=+2.1 (c 0.13, MeOH) [calculated for the corresponding trifluoroacetate salt].

Example 5

(−)6-(ethylamino)-4-(4-fluorophenyl)-3,4-dihydro-1,3,5-triazin-2(1H)-one

The title compound was obtained, as a white solid, by chiral HPLC enantiomeric separation of the racemic compound of Example 3: 0.043 g (57%). ee>99.4% (detector UV 240 nm). Retention time on analytical chiral HPLC: 16.479 min. $^1$H-NMR ($CD_3OD$, 400 MHz) δ 1.11 (t, J=8.0, 3H), 3.20 (q, J=8.0, 2H), 5.65 (s, 1H), 7.06-7.10 (m, 2H), 7.40-7.43 (m, 2H). $^{13}$C-NMR ($CD_3OD$, 100 MHz) δ 14.9, 36.7, 67.5, 116.3 (d, J=22.0), 129.5 (d, J=8.0), 139.6, 156.6, 158.5, 164.2 (d, J=244.0). MS (ESI) m/z: 237 [M+H]$^+$; MS (ESI) m/z: 235 [M−H]$^-$. $[\alpha]^{20}_D$=−0.9 (c 0.13, MeOH) [calculated for the corresponding trifluoroacetate salt].

Example 6

4-(4-fluorophenyl)-6-(propylamino)-3,4-dihydro-1,3,5-triazin-2(1H)-one

The title compound was obtained according to general procedure C using 4-fluoro-benzaldheyde (IIa) (0.36 mL, 3.32 mmol) and IIIc (0.40 g, 2.77 mmol). Elution with DCM/MeOH/33% aqueous $NH_3$ solution (9:1:0.1) afforded the compound of example 6 as a white solid: 0.11 g (16%). $^1$H-NMR (DMSO-$d_6$, 400 MHz) δ 0.84 (t, J=7.2, 3H), 1.40-1.49 (m, 2H), 3.03 (t, J=6.0, 2H), 5.59 (s, 1H), 5.75 (br s, exch, 1H), 7.14-7.18 (m, 2H), 7.34-7.38 (m, 2H), 7.55 (br s, exch, 1H), 8.55 (br s, exch, 1H). $^{13}$C-NMR (DMSO-$d_6$, 100 MHz) δ 11.8, 22.7, 42.3, 68.1, 115.4 (d, J=22.0), 128.6 (d, J=8.0), 141.2, 149.0, 153.8, 161.6 (d, J=244.0). MS (ESI) m/z: 251 [M+H]$^+$.

Example 7

4-(4-fluorophenyl)-6-(isopropylamino)-3,4-dihydro-1,3,5-triazin-2(1H)-one

The title compound was obtained according to general procedure C using 4-fluoro-benzaldheyde (IIa) (0.45 mL, 4.15 mmol) and IIId (0.50 g, 3.46 mmol). Trituration with a mixture of organic solvents (DCM/Et$_2$O) afforded the compound of example 7 as a white solid: 0.19 g (22%). $^1$H-NMR (CD$_3$OD, 400 MHz) δ 1.11 (m, 6H), 3.81-3.92 (m, 1H), 5.65 (s, 1H), 7.08-7.12 (m, 2H), 7.41-7.45 (m, 2H). $^{13}$C-NMR (CD$_3$OD, 100 MHz) δ 21.6, 21.7, 42.1, 65.5, 114.9 (d, J=20.5), 128.1 (d, J=8.3), 138.6, 150.5, 154.6, 164.2 (d, J=242.0). MS (ESI) m/z: 251 [M+H]$^+$; MS (ESI) m/z: 249 [M−H]$^−$.

Example 8

4-(4-fluorophenyl)-6-(isobutylamino)-3,4-dihydro-1,3,5-triazin-2(1H)-one

The title compound was obtained according to general procedure C using 4-fluoro-benzaldheyde (IIa) (1.13 mL, 10.52 mmol) and IIIe (1.34 g, 8.77 mmol). Elution with DCM/MeOH/33% aqueous NH$_3$ solution (9:1:0.05) afforded the compound of example 8 as a white solid: 0.33 g (14%). $^1$H-NMR (CD$_3$OD, 400 MHz) δ 0.91 (d, J=6.8, 6H), 1.79-1.82 (m, 1H), 3.00-3.05 (m, 2H), 5.69 (s, 1H), 7.08-7.12 (m, 2H), 7.43-7.46 (m, 2H). $^{13}$C-NMR (CD$_3$OD, 100 MHz) δ 19.1, 28.1, 66.0, 115.0 (d, J=21.2), 128.1 (d, J=8.3), 138.2, 149.2, 153.8, 162.8 (d, J=243.8). MS (ESI) m/z: 265 [M+H]$^+$; MS (ESI) m/z: 263 [M−H]$^−$.

Example 9

4-(4-fluorophenyl)-6-(phenylamino)-3,4-dihydro-1,3,5-triazin-2(1H)-one

The title compound was obtained according to general procedure C using 4-fluoro-benzaldheyde (IIa) (0.30 mL, 2.70 mmol) and IIIf (0.40 g, 2.24 mmol). Elution with DCM/MeOH (9:1) afforded the compound of example 9 as a white solid: 0.06 g (10%). $^1$H-NMR (DMSO-d$_6$, 400 MHz) δ 5.78 (s, 1H), 6.89-6.92 (m, 1H), 7.17-7.24 (m, 4H), 7.41-7.45 (m, 2H), 7.52-7.54 (m, 2H), 7.82 (br s, exch, 1H), 8.02 (br s, exch, 1H), 8.52 (br s, exch, 1H). $^{13}$C-NMR (DMSO-d$_6$, 100 MHz) δ 68.3, 114.6 (d, J=21.0), 118.1, 121.3, 128.2 (d, J=9.0), 128.6, 140.0, 145.11, 145.6, 152.1, 162.0 (d, J=240.2). MS (ESI) m/z: 285 [M+H]$^+$; MS (ESI) m/z: 283 [M−H]$^−$.

Example 10

6-(dimethylamino)-4-(4-fluorophenyl)-3,4-dihydro-1,3,5-triazin-2(1H)-one

The title compound was obtained according to general procedure C using 4-fluoro-benzaldheyde (IIa) (0.45 mL, 4.25 mmol) and IIIg (0.46 g, 3.54 mmol). Elution with DCM/MeOH/33% aqueous NH$_3$ solution (8.5:1.5:0.1) afforded the compound of example 10 as a white solid: 0.11 g (13%). $^1$H-NMR (CD$_3$OD, 400 MHz) δ 3.02 (s, 6H), 5.67 (s, 1H), 7.11-7.15 (m, 2H), 7.45-7.49 (m, 2H). $^{13}$C-NMR (CD$_3$OD, 100 MHz) δ 36.0, 66.2, 115.0 (d, J=21.2), 128.1 (d, J=9.1), 139.2, 153.6, 155.6, 162.9 (d, J=244.0). MS (ESI) m/z: 237 [M+H]$^+$; MS (ESI) m/z: 235 [M−H]$^−$.

Example 11

6-(diethylamino)-4-(4-fluorophenyl)-3,4-dihydro-1,3,5-triazin-2(1H)-one

The title compound was obtained according to general procedure C using 4-fluoro-benzaldheyde (IIa) (0.59 mL, 5.52 mmol) and IIIh (0.73 g, 4.60 mmol). Trituration with a mixture of organic solvents (DCM/Et$_2$O) afforded the compound of example 11 as a white solid: 0.25 g (21%). $^1$H-NMR (CD$_3$OD, 400 MHz) δ 1.12 (t, J=7.0, 6H), 3.42 (q, J=7.0, 4H), 5.66 (s, 1H), 7.07-7.12 (m, 2H), 7.43-7.46 (m, 2H). $^{13}$C-NMR (CD$_3$OD, 100 MHz) δ 12.3, 41.5, 64.7, 115.0 (d, J=21.2), 128.0 (d, J=8.4), 137.9, 150.8, 153.7, 162.9 (d, J=243.3). MS (ESI) m/z: 265 [M+H]$^+$; MS (ESI) m/z: 263 [M−H]$^−$.

Example 12

4-(4-fluorophenyl)-6-(piperidin-1-yl)-3,4-dihydro-1,3,5-triazin-2(1H)-one

The title compound was obtained according to general procedure C using 4-fluoro-benzaldheyde (IIa) (0.40 mL, 3.62 mmol) and IIIi (0.51 g, 3.02 mmol). Elution with DCM/MeOH/33% aqueous NH$_3$ solution (9:1:0.05) afforded the compound of example 12 as a white solid: 0.23 g (28%). $^1$H-NMR (CD$_3$OD, 400 MHz) δ 1.55-1.58 (m, 4H), 1.64-1.68 (m, 2H), 3.49-3.52 (m, 4H), 5.67 (s, 1H), 7.10-7.14 (m, 2H), 7.44-7.48 (m, 2H). $^{13}$C-NMR (CD$_3$OD, 100 MHz) δ 23.9, 25.4, 45.6, 64.5, 115.0 (d, J=22.0), 128.1 (d, J=8.3), 137.5 (d, J=3.9), 151.8, 156.0, 164.3 (d, J=243.8). MS (ESI) m/z: 277 [M+H]$^+$; MS (ESI) m/z: 275 [M−H]$^−$.

Example 13

6-(butylamino)-4-(4-fluorophenyl)-3,4-dihydro-1,3,5-triazin-2(1H)-one

The title compound was obtained according to general procedure C using 4-fluoro-benzaldheyde (IIa) (0.94 mL, 8.76 mmol) and IIIj (1.15 g, 7.30 mmol). Elution with DCM/MeOH/33% aqueous NH$_3$ solution (9:1:0.1) afforded the compound of example 13 as a white solid: 0.71 g (39%). $^1$H-NMR (CD$_3$OD, 400 MHz) δ 0.88-0.92 (m, 3H), 1.32-1.36 (m, 2H), 1.48-1.54 (m, 2H), 3.17-3-18 (m, 2H), 5.70 (s, 1H), 7.06-7.11 (m, 2H), 7.43-7.46 (m, 2H). $^{13}$C-NMR (CD$_3$OD, 100 MHz) δ 14.2, 21.0, 32.4, 41.6, 67.1, 116.3 (d, J=21.9), 129.4 (d, J=8.4), 139.3, 151.3, 155.2, 163.7 (d, J=243.8). MS (ESI) m/z: 265 [M+H]$^+$; MS (ESI) m/z: 263 [M−H]$^−$.

Example 14

6-(ethylamino)-4-(pyridin-3-yl)-3,4-dihydro-1,3,5-triazin-2(1H)-one

The title compound was obtained according to general procedure C using 3-pyridinecarboxaldehyde (IIc) (0.43 mL, 4.61 mmol) and IIIb (0.50 g, 3.84 mmol). Elution with DCM/MeOH/33% aqueous NH$_3$ solution (8:2:0.2) afforded the compound of example 14 as a white solid: 0.08 g (10%). $^1$H-NMR (CD$_3$OD, 400 MHz) δ 1.40 (t, J=6.8, 3H), 3.19 (q, J=6.8, 2H), 5.79 (s, 1H), 7.44-7.47 (m, 1H), 7.89 (d, J=8.5, 1H), 8.50 (d, J=5.0, 1H), 8.58 (s, 1H). $^{13}$C-NMR (CD$_3$OD, 100 MHz) δ 13.4, 35.3, 65.0, 124.0, 134.9, 138.5, 147.2, 148.8, 151.3, 155.2. MS (ESI) m/z: 220 [M+H]$^+$; MS (ESI) m/z: 218 [M−H]$^−$.

Example 15

4-(4-fluorophenyl)-6-(pyrrolidin-1-yl)-3,4-dihydro-1,3,5-triazin-2(1H)-one

The title compound was obtained according to general procedure C using 4-fluoro-benzaldheyde (IIa) (0.65 mL, 6.10 mmol) and IIIk (0.80 g, 5.08 mmol). Elution with DCM/MeOH/33% aqueous $NH_3$ solution (9:1:0.05) afforded the compound of example 15 as a white solid: 0.29 g (22%). $^1$H-NMR (CD$_3$OD, 400 MHz) δ 1.91-1.93 (m, 4H), 3.40-3.43 (m, 4H), 5.69 (s, 1H), 7.08-7.13 (m, 2H), 7.46-7.49 (m, 2H). $^{13}$C-NMR (CD$_3$OD, 100 MHz) δ 24.7, 46.3, 64.8, 115.0 (d, J=21.2), 128.3 (d, J=8.3), 137.7, 155.3, 160.4, 163.5 (d, J=244.4). MS (ESI) m/z: 263 [M+H]$^+$.

Preparation II (Examples 16-21)

General synthesis of compounds of Formula (I) wherein $R_1$ is hydrogen, linear or branched unsubstituted or substituted $C_{1-6}$alkyl, $R_2$ is $COR_5$, and $R_3$, $R_4$, $R_5$, $Y_1$ and $Y_2$ are as defined in Formula (I).

General Procedure (D): Synthesis of Intermediates of Formula (VIII)—Steps 1-3, Scheme 1

Intermediates of Formula (VIII) were obtained according to the procedures reported in preparation I, following Steps 1-3 in Scheme 1.

(VIIIa) 6-amino-4-(4-fluorophenyl)-3,4-dihydro-1,3,5-triazin-2(1H)-one

The title compound was obtained according to general procedure D using 4-fluoro-benzaldheyde (IIa) (2.5 mL, 23.80 mmol) and the commercially available guanylurea sulphate (3.0 g, 19.80 mmol). Trituration with a mixture of organic solvents (DCM/MeOH) afforded VIIIa as a white solid: 2.90 g (88%). $^1$H-NMR (DMSO-d$_6$, 400 MHz) δ 5.56 (s, 1H), 5.75 (br s, exch, 1H) 7.15-7.19 (m, 2H), 7.35-7.38 (m, 2H), 7.49 (br s, exch, 1H), 8.51 (br s, exch, 1H). $^{13}$C-NMR (DMSO-d$_6$, 100 MHz) δ 67.5, 115.4 (d, J=22.0), 128.6 (d, J=8.0), 140.2, 150.8, 153.5, 161.2 (d, J=244.0). MS (ESI) m/z: 209 [M+H]$^+$.

General Procedure (E): Synthesis of Compounds of Formula (I)—Scheme 2

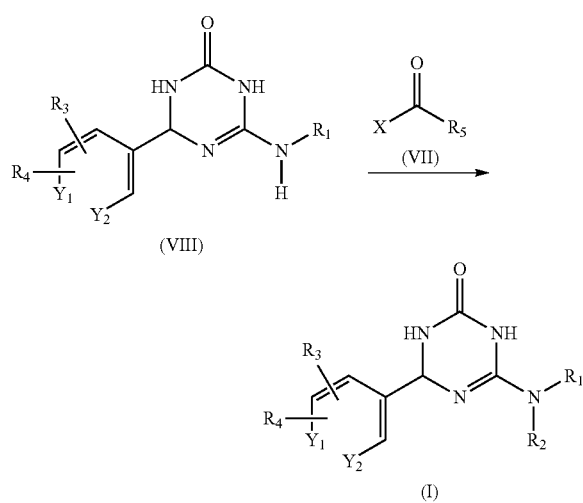

Scheme 2

(VIII)

(I)

Method (a): To an ice-cold solution/suspension of VIII (1 eq.) in a mixture of organic solvent such as pyridine/DCM, DMF/DCM, and 2,6-lutidine/DMF (0.4 M) was added dropwise the proper acyl chloride (VII) (1 eq.). After stirring at 0° C. for 3-4 hours, the reaction mixture was diluted with DCM or EtOAc and washed with 2N HCl. The organic phase was dried over anhydrous Na$_2$SO$_4$ and evaporated under reduced pressure. The crude triazinone (I) was purified by flash chromatography.

Method (b): A solution of the proper carboxylic acid (VII) (1 eq.) and EDCI.HCl (1.3), in DCM or DMF (0.15 M), was treated with HOBt (1.3 eq.). The mixture was stirred for 1 h at rt, and then added dropwise to an ice-cold suspension of VIII (1.1 eq.) in DCM or DMF (0.12 M). After adding Et$_3$N or DIPEA (1.1 eq.), the resulting mixture was allowed to stir overnight at rt.

The reaction mixture was then either diluted with DCM and washed with H$_2$O, or diluted with EtOAc and washed with 5% aqueous LiCl solution, in case the reaction solvent was DCM or DMF respectively. The organic phase was dried over anhydrous Na$_2$SO$_4$ and evaporated under reduced pressure. The crude triazinone (I) was purified by flash chromatography.

Method (c): A solution of the proper carboxylic acid (VII) (1.2 eq.) and EDCI.HCl (1.56), in DMF (0.4 M), was stirred for 1 hour at rt, and then added dropwise to an ice-cold suspension of VIII (1 eq.) in DMF (0.12 M). After stirring overnight at rt, the reaction mixture was diluted with EtOAc and washed with 5% aqueous LiCl solution. The organic phase was dried over anhydrous Na$_2$SO$_4$ and evaporated under reduced pressure. The residue was then triturated with organic solvents, affording the compound of interest without further purification.

Example 16

N-(4-(4-fluorophenyl)-6-oxo-1,4,5,6-tetrahydro-1,3,5-triazin-2-yl)acetamide

The title compound was obtained according to general procedure E, method (a), from VIIIa (0.08 g, 0.38 mmol) and AcCl (27 μL, 0.38 mmol) in 2,6-lutidine/DMF (3:1). Elution with DCM/MeOH (9.5:0.5) afforded the compound of example 15 as a white solid: 24 mg (25%). $^1$H-NMR (DMSO-d$_6$, 400 MHz) δ 1.98 (s, 3H), 5.74 (s, 1H), 7.13-7.17 (m, 2H), 7.33-7.36 (m, 2H), 7.96 (br s, exch, 1H). $^{13}$C-NMR (DMSO-d$_6$, 100 MHz) δ 23.8, 67.2, 114.8 (d, J=22.0), 127.3 (d, J=8.0), 139.6, 146.9, 152.3, 161.2 (d, J=244.0), 174.8. MS (ESI) m/z: 251 [M+H]$^+$; MS (ESI) m/z: 249 [M−H]$^-$.

Example 17

N-(4-(4-fluorophenyl)-6-oxo-1,4,5,6-tetrahydro-1,3,5-triazin-2-yl)-2-propylpentanamide The title compound was obtained according to general procedure E, method (b), from VIIIa (0.15 g, 0.72 mmol) and valproic acid (104 μL, 0.65 mmol) in DMF. Elution with DCM/MeOH (9.5:0.5) afforded the compound of example 16 as a white solid: 80 mg (37%). $^1$H-NMR (DMSO-d$_6$, 400 MHz) δ 0.81-0.85 (m, 6H), 1.19-1.25 (m, 4H) 1.26-1.35 (m, 2H), 1.45-1.54 (m, 2H), 2.35-2.37 (m, 1H), 5.78 (s, 1H), 7.18-7.20 (m, 2H), 7.35-7.37 (m, 2H), 7.95 (br s, exch, 1H), 9.84 (br s, exch, 1H), 10.76 (br s, exch, 1H). $^{13}$C-NMR (DMSO-d$_6$, 100 MHz) δ 14.0, 20.5, 34.7, 47.3, 68.2, 115.5 (d, J=21.0), 127.5 (d, J=8.3), 139.3, 145.6, 152.3, 162.5 (d, J=247.3), 180.0. MS (ESI) m/z: 335 [M+H]$^+$; MS (ESI) m/z: 333 [M−H]$^-$.

Example 18

5-(1,2-dithiolan-3-yl)-N-(4-(4-fluorophenyl)-6-oxo-1,4,5,6-tetrahydro-1,3,5-triazin-2-yl)pentanamide The title compound was obtained according to general procedure E, method (b), from VIIIa (0.15 g, 0.72 mmol) and (+/−) lipoic acid (0.13 g, 0.65 mmol) in DCM. Elution with DCM/MeOH (9.5:0.5) afforded the compound of example 17 as a white solid: 77 mg (31%). $^1$H-NMR (DMSO-d$_6$, 400 MHz) δ 1.33-1.39 (m, 2H), 1.49-1.59 (m, 3H), 1.62-1.70 (m, 1H), 1.82-1.90 (m, 1H), 2.31 (t, J=4.0, 2H), 2.36-2.44 (m, 1H), 3.08-3.14 (m, 1H), 3.15-3.21 (m, 1H), 3.58-3.66 (m, 1H) 5.80 (s, 1H), 7.18-7.23 (m, 2H), 7.39-7.42 (m, 2H) 8.00 (br s, exch, 1H), 9.88 (br s, exch, 1H), 10.65 (br s, exch, 1H). $^{13}$C-NMR (DMSO-d$_6$, 100 MHz) δ 24.2, 27.9, 33.9, 36.2, 38.0, 39.7, 55.9, 67.5, 115.1 (d, J=21.0), 128.0 (d, J=8.3), 139.2, 145.6, 151.2, 162.1 (d, J=243.0), 176.8. MS (ESI) m/z: 397 [M+H]$^+$; MS (ESI) m/z: 395 [M−H]$^-$

Example 19

3-((1H-benzo[d][1,2,3]triazol-1-yl)oxy)-N-(4-(4-fluorophenyl)-6-oxo-1,4,5,6-tetrahydro-1,3,5-triazin-2-yl)propanamide The title compound was obtained according to general procedure E, method (b), from VIIIa (0.10 g, 0.48 mmol) and acrylic acid (33 µL, 0.48 mmol) in DMF. After stirring at rt overnight, precipitation of a white solid was observed. The precipitate was collected by filtration and triturate with a mixture of DCM/Et$_2$O, affording the compound of interest as a white solid: 45 mg (25%). $^1$H-NMR (DMSO-d$_6$, 400 MHz) δ 2.98-3.01 (m, 2H), 4.69-4.71 (m, 2H), 5.79 (s, 1H), 7.19-7.24 (m, 2H), 7.35-7.38 (m, 2H), 7.41-7.45 (m, 1H), 7.66-7.70 (m, 1H), 7.86 (d, J=8.8, 1H), 7.93 (d, J=8.4, 1H), 8.15 (br, exch, 1H), 9.74 (br, exch, 1H), 10.62 (br, exch, 1H). $^{13}$C-NMR (DMSO-d$_6$, 100 MHz) δ 30.5, 43.6, 67.5, 112.5, 114.7, 115.3 (d, J=21.0), 124.4, 128.1 (d, J=9.0), 130.3, 133.9, 134.0, 137.8, 147.8, 150.5, 161.8 (d, J=246), 175.3. MS (ESI) m/z: 398 [M+H]$^+$; MS (ESI) m/z: 396 [M−H]$^-$.

Example 20

N-(4-(4-fluorophenyl)-6-oxo-1,4,5,6-tetrahydro-1,3,5-triazin-2-yl)-2-phenoxyacetamide The title compound was obtained according to general procedure E, method (c), from VIIIa (0.20 g, 0.96 mmol) and phenoxy acetic acid (0.18 g, 1.15 mmol). Triturate with a mixture of DCM/Et$_2$O afforded the compound of example 19 as a white solid: 11 mg (3%). $^1$H-NMR (CD$_3$OD, 400 MHz) δ 4.64 (s, 2H), 5.90 (s, 1H), 6.94-6.96 (m, 3H), 7.13-7.17 (m, 2H), 7.25-7.28 (m, 2H), 7.45-7.48 (m, 2H). MS (ESI) m/z: 343 [M+H]$^+$; MS (ESI) m/z: 341 [M−H]$^-$.

Example 21

2-(4-fluorophenoxy)-N-(4-(4-fluorophenyl)-6-oxo-1,4,5,6-tetrahydro-1,3,5-triazin-2-yl)acetamide The title compound was obtained according to general procedure E, method (c), from VIIIa (0.16 g, 0.78 mmol) and 4-fluorophenoxy acetic acid (0.16 g, 0.94 mmol). Trituration with a mixture of DCM/Et$_2$O afforded the compound of example 20 as a white solid: 34 mg (12%). $^1$H-NMR (DMSO-d$_6$, 400 MHz) δ 4.57 (s, 2H), 5.78 (s, 1H), 6.84-6.87 (m, 2H), 7.04-7.08 (m, 2H), 7.20-7.24 (m, 2H), 7.37-7.40 (m, 2H), 8.42 (br s, exch, 1H), 10.38 (br s, exch, 1H). $^{13}$C-NMR (DMSO-d$_6$, 100 MHz) δ 64.4, 69.0, 115.3, 115.6, 115.7, 127.8, 137.1, 147.6, 151.0, 154.6, 155.8 (d, J=260), 162.0 (d, J=244), 172.7. MS (ESI) m/z: 361 [M+H]$^+$; MS (ESI) m/z: 359 [M−H]$^-$.

Example 22

6-((3-(dimethylamino)propyl)amino)-4-(4-fluorophenyl)-3,4-dihydro-1,3,5-triazin-2(1H)-one The title compound was obtained according to general procedure C using 4-F-benzaldehyde (IIa) (78 µL, 0.72 mmol) and IIIl (0.10 g, 0.60 mmol). Elution with DCM/MeOH/33% aqueous NH$_3$ solution (7.5:2.5:0.2.5) afforded the compound of example 22 as a white solid: 30 mg (17%). $^1$H-NMR (CD$_3$OD, 400 MHz) δ1.69-1.73 (m, 2H), 2.22 (s, 6H), 2.38 (t, J=7.2, 2H), 3.21-3.28 (m, 2H), 5.67 (s, 1H), 7.08-7.13 (m, 2H), 7.42-7.46 (m, 2H). $^{13}$C-NMR (CD$_3$OD, 100 MHz) δ 25.8, 38.6, 46.2, 55.8, 66.0, 115.3 (d, J=21.6) 128.5 (d, J=8.7), 139.5, 150.6, 152.7, 162.3 (d, J=242.8). MS (ESI) m/z 294 [M+H]$^+$; MS (ESI) m/z 292 [M−H]$^-$.

Example 23

4-(4-fluorophenyl)-6-((3-(piperidin-1-yl)propyl)amino)-3,4-dihydro-1,3,5-triazin-2(1H)-one The title compound was obtained according to general procedure C using 4-F-benzaldehyde (IIa) (0.20 mL, 1.80 mmol) and IIIm (0.34 g, 1.50 mmol). Elution with DCM/MeOH/33% aqueous NH$_3$ solution (7.5:2.5:0.2.5) afforded the compound of example 23 as a white solid: 0.12 g (24%). $^1$H-NMR (CD$_3$OD, 400 MHz) δ 1.44-1.46 (m, 2H), 1.56-1.60 (m, 4H), 1.70-1.74 (m, 2H), 2.37-2.44 (m, 6H), 3.20-3.23 (m, 2H), 5.65 (s, 1H), 7.07-7.11 (m, 2H), 7.40-7.44 (m, 2H). $^{13}$C-NMR (CD$_3$OD, 100 MHz) δ 23.6, 24.9, 25.8, 38.6, 53.9, 55.8, 66.0, 115.0 (d, J=21.2), 128.1 (d, J=8.4), 138.2, 150.3, 153.2, 162.7 (d, J=243.8). MS (ESI) m/z 334 [M+H]$^+$; MS (ESI) m/z 332 [M−H]$^-$.

Example 24

6-(benzylamino)-4-(4-fluorophenyl)-3,4-dihydro-1,3,5-triazin-2(1H)-one

The title compound was obtained according to general procedure C using 4-F-benzaldehyde (IIa) (0.56 mL, 5.20 mmol) and IIIn (0.82 g, 4.30 mmol). Elution with DCM/MeOH/33% aqueous NH$_3$ solution (9:1:0.1) afforded the compound of example 24 as a white solid: 0.12 g (36%). $^1$H-NMR (DMSO-d$_6$, 400 MHz) δ 4.40-4.44 (m, 2H), 5.71 (s, 1H), 7.06-7.11 (m, 2H), 7.26-7.31 (m, 7H). $^{13}$C-NMR (DMSO-d$_6$, 100 MHz) δ 44.5, 67.3, 114.9 (d, J=21.2), 126.7, 127.0 (d, J=8.3), 128.06, 128.1, 138.3, 142.7, 150.6, 152.8, 162.5 (d, J=242.6). MS (ESI) m/z 299 [M+H]$^+$; MS (ESI) m/z 297 [M−H]$^-$.

Example 25

4-(4-fluorophenyl)-6-((pyridin-4-ylmethyl)amino)-3,4-dihydro-1,3,5-triazin-2(1H)-one The title compound was obtained according to general procedure C using 4-F-benzaldehyde (IIa) (0.58 mL, 5350 mmol) and IIIo (0.86 g, 4.46 mmol). Elution with DCM/MeOH/33% aqueous NH$_3$ solution (8:2:0.2) afforded the compound of example 25 as a white solid: 0.18 g (14%). $^1$H-NMR (DMSO-d$_6$, 400 MHz) δ 4.35 (s, 2H), 5.59 (s, 1H), 7.08-7.13 (m, 2H), 7.24-7.26 (m, 4H), 8.47 (d, J=4.8, 2H). $^{13}$C-NMR (DMSO-d$_6$, 100 MHz) δ 42.4, 67.1, 114.5 (d, J=21.3), 121.8, 127.9 (d, J=8.2), 139.4, 148.6, 149.1, 152.5, 153.2, 161.3 (d, J=250.0). MS (ESI) m/z 300 [M+H]$^+$; MS (ESI) m/z 298 [M−H]$^-$.

Example 26

6-(dipropylamino)-4-(4-fluorophenyl)-3,4-dihydro-1,3,5-triazin-2(1H)-one

The title compound was obtained according to general procedure C using 4-fluoro-benzaldheyde (IIa) (0.47 mL, 4.38 mmol) and IIIp (0.68 g, 3.64 mmol). Trituration with a mixture of organic solvents (DCM/Et$_2$O) afforded the compound of example 26 as a white solid: 0.23 g (22%). $^1$H-NMR (CD$_3$OD, 400 MHz) δ 0.88 (t, J=7.2, 6H), 1.55-1.61 (m, 4H), 3.27-3.30 (m, 2H), 3.36-3.41 (m, 2H), 5.65 (s, 1H), 7.10-7.14 (m, 2H), 7.43-7.47 (m, 2H). $^{13}$C-NMR (CD$_3$OD, 100 MHz) δ 9.8, 20.8, 48.8, 64.6, 115.0 (d, J=22.0), 128.0 (d, J=9.0), 137.9, 156.7, 161.2, 162.9 (d, J=243). MS (ESI) m/z 293 [M+H]$^+$; MS (ESI) m/z 291 [M−H]$^-$.

Methods to Assess the Biochemical Activity of the Compounds of the Invention

Inhibition of BACE-1

β-secretase (BACE-1, Sigma-Aldrich) inhibition studies were performed by employing a peptide mimicking APP sequence as substrate (Methoxycoumarin-Ser-Glu-Val-Asn-Leu-Asp-Ala-Glu-Phe-Lys-dinitrophenyl, M-2420, Bachem, Germany). The following procedure was employed: 5 μL of test compounds (or DMSO, if preparing a control well) were pre-incubated with 175 μL of enzyme (in 20 mM sodium acetate containing 3-[(3-Cholamidopropyl)dimethylammonio]-1-propanesulfonate (CHAPS) 0.1% w/v) for 1 hour at rt. The substrate (3 μM, final concentration) was then added and left to react for 15 minutes at 37° C. The fluorescence signal was read at λem=405 nm (λexc=320 nm) using a Fluoroskan Ascent. The DMSO concentration in the final mixture maintained below 5% (v/v) guaranteed no significant loss of enzyme activity. The fluorescence intensities with and without inhibitor were compared and the percent inhibition due to the presence of test compounds was calculated. The background signal was measured in control wells containing all the reagents, except BACE-1 and subtracted. The % inhibition due to the presence of increasing test compound concentration was calculated by the following expression: 100−(IF$_i$/IF$_o$×100) where IF$_i$ and IF$_o$ are the fluorescence intensities obtained for BACE-1 in the presence and in the absence of inhibitor, respectively. Inhibition curves were obtained by plotting the % inhibition versus the logarithm of inhibitor concentration in the assay sample, when possible. The linear regression parameters were determined and the IC$_{50}$ extrapolated (GraphPad Prism 4.0, GraphPad Software Inc.). To demonstrate inhibition of BACE-1 activity a peptido-mimetic inhibitor (β-secretase inhibitor IV, Calbiochem, IC$_{50}$=20 nM) was serially diluted into the reactions' wells. The results are illustrated in Table 1.

Inhibition of GSK-3β

Human recombinant GSK-3β was purchased from Millipore (Millipore Iberica S.A.U.) The prephosphorylated polypeptide substrate was purchased from Millipore (Millipore Iberica SAU). Kinase-Glo Luminescent Kinase Assay was obtained from Promega (Promega Biotech Iberica, SL). ATP and all other reagents were from Sigma-Aldrich. Assay buffer contained 50 mM 4-(2-hydroxyethyl)-1-piperazineethanesulfonic acid (HEPES) (pH 7.5), 1 mM ethylenediaminetetraacetic acid (EDTA), 1 mM ethylene glycol tetraacetic acid (EGTA), and 15 mM magnesium acetate. The method developed by Baki was followed [Baki et al. Assay and Drug Development Technologies 2007, 5(1),75-83] to analyze the inhibition of GSK-3β. Kinase-Glo assays were performed in assay buffer using white 96-well plates. In a typical assay, 10 μL (10 μM) of test compound (dissolved in DMSO at 1 mM concentration and diluted in advance in assay buffer to the desired concentration) and 10 μL (20 ng) of enzyme were added to each well followed by 20 μL of assay buffer containing 25 μM substrate and 1 μM adenosine triphosphate (ATP). The final DMSO concentration in the reaction mixture did not exceed 1%. After a 30 minutes incubation at 30° C., the enzymatic reaction was stopped with 40 μL of Kinase-Glo reagent. Glow-type luminescence was recorded after 10 minutes using a Fluoroskan Ascent multimode reader.

The activity is proportional to the difference of the total and consumed ATP. The inhibitory activities were calculated on the basis of maximal kinase (AVERAGE positive) and luciferase activities (AVERAGE negative) measured in the absence of inhibitor and in the presence of reference compound inhibitor (SB415826 [Coghlan et al. Chem Biol 2000, 7, 793-803], Merck Millipore, IC$_{50}$=54 nM) at total inhibition concentration (5 μM), respectively.

The linear regression parameters were determined and the IC$_{50}$ extrapolated (GraphPad Prism 4.0, GraphPad Software Inc.). The results are illustrated in Table 1.

TABLE 1

| Example | BACE-1 IC$_{50}$ (μM) | GSK-3β IC$_{50}$ (μM) |
|---|---|---|
| 2 | 50.31 ± 6.61 | 40.71 ± 2.70 |
| 3 | 16.05 ± 0.64 | 7.11 ± 0.37 |
| 4 | 8.13 | 12.57 |
| 5 | 12.55 | 15.67 |
| 6 | 36.83 ± 9.85 | 4.34 ± 0.63 |
| 9 | n.a. | 6.93 ± 0.14 | n.a.: not available

Methods to Assess the Neuroprotective Activity of the Compounds of the Invention Primary Cell Cultures Astrocytes were prepared from neonatal (P2) rat cerebral cortex, as previously described by Luna-Medina et al. [Luna-Medina, R.; Cortes-Canteli, M.; Alonso, M.; Santos, A.; Martinez, A.; Perez-Castillo, A. Regulation of inflammatory response in neural cells in vitro by thiadiazolidinones derivatives through peroxisome proliferator-activated receptor gamma activation. J. Biol. Chem. 2005, 280, 21453-21462].

Briefly, after removal of the meninges, the cerebral cortex was dissected, dissociated, and incubated with 0.25% trypsin/EDTA at 37° C. for 1 hour. After centrifugation, the pellet was washed 3 times with Hank's balanced salt solution (HBSS) (Gibco) and the cells were placed on noncoated flasks and maintained in HAMS/Dulbecco's modified eagle's medium (DMEM) (1:1) medium containing 10% of fetal bovine serum (FBS). After 15 days, the flasks were agitated on an orbital shaker for 4 hours at 240 rpm at 37° C., the supernatant was collected, centrifuged, and the cellular pellet containing the microglial cells resuspended in complete medium (HAMS/DMEM (1:1) containing 10% FBS) and seeded on uncoated 96-well plates. Cells were allowed to adhere for 2 hours, and the medium was removed to eliminate nonadherent oligodendrocytes. New fresh medium containing 10 ng/mL of granulocyte-macrophage colony-stimulating factor (GM-CSF) was added. The remaining astroglial cells adhered on the flasks were then trypsinized, collected, centrifugated, and plated onto 96-well plates with complete medium. The purity of cultures obtained by this procedure was >98% as determined by immunofluorescence with the OX42 (microglial marker) and the glial fibrillary acidic protein (GFAP, astroglial marker) antibodies.

Nitrites Measurement

An overexpression and/or over activity of GSK-3β results in increased level of microglia activation in different neurodegenerative diseases. Furthermore, GSK-3β is proved to regulate inflammatory tolerance in astrocytes [Beurel, E.; Jope, R. S. Glycogen synthase kinase-3 regulates inflammatory tolerance in astrocytes. Neuroscience 2011, 169, 1063-1070]. Accordingly, we explored whether these new BACE-1/GSK-3β dual inhibitors, might exert anti-inflammatory effect in cell-based assays.

The potential anti-inflammatory activity of the selected compounds was tested by evaluating the production of nitrites from primary cultured glial cells. Primary cultures of astrocytes and microglia were incubated with the selected compounds (10 μM) for 1 hour, and then cells were cultured for another 24 hours with a potent inflammatory agent, such as lipopolysaccharide (LPS) (10 μg/mL). LPS is able to induce nitrite production and accumulation in the culture medium, which was assayed by the standard Griess reaction. Supernatants were collected from the media and mixed with an equal volume of Griess reagent (Sigma). Samples were then incubated at rt for 15 minutes and absorbance read using a plate reader at 492/540 nm.

Figure 2B:
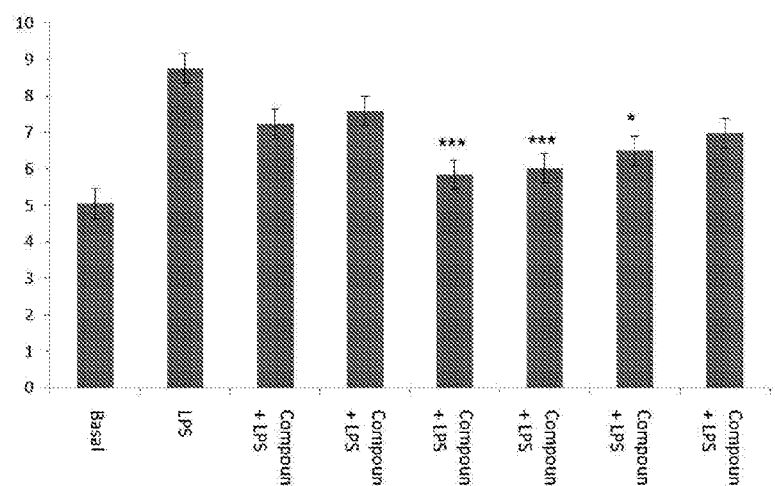

When primary astrocytes and microglial cells were stimulated with LPS, we observed a significant induction of nitrite production, which was generally reduced by triazinones treatment (FIGS. 2A, 2B). Particularly, the 6-(alkylamino) and 6-(phenylamino) compounds of examples 3, 6 and 9 normally showed a higher potency than the 6-amino triazinones, used as reference compounds (compounds A-C in Table 2 below). More interestingly, compounds of example 3 and 6, showing a balanced GSK-3β/BACE-1 inhibitory profile, resulted the most potent among the tested derivatives, and they were able to restore nitrite production to basal level in astrocyte cells (FIG. 2A).

Methods to Assess the Neurogenic Activity of the Compounds of the Invention

Neurosphere Cultures

Neurosphere (NS) cultures were derived from the hippocampus of adult rats and induced to proliferate using established passaging methods to achieve optimal cellular expansion according to published protocols [Ferron, S. R.; Andreu-Agullo, C.; Mira, H.; Sanchez, P.; Marques-Torrejon, M. A.; Farinas, I. A combined ex/in vivo assay to detect effects of exogenously added factors in neural stem cells. Nature Protoc. 2007, 2, 849-859]. Rats were decapitated, brains removed, and the hippocampus dissected as described [Morales-Garcia, J. A.; Luna-Medina, R.; Alfaro-Cervello, C.; Cortes-Canteli, M.; Santos, A.; Garcia-Verdugo, J. M.; Perez-Castillo, A. Peroxisome proliferator-activated receptor gamma ligands regulate neural stem cell proliferation and differentiation in vitro and in vivo. Glia 2011, 59, 293-307]. Briefly, cells were seeded into 12-well dishes and cultured in DMEM/F12 (1:1, Invitrogen) containing 10 ng/mL epidermal growth factor (EGF, Peprotech, London, UK), 10 ng/mL fibroblast growth factor (FGF, Peprotech), and B27 medium (Gibco). After 3 days in culture, NS were cultivated in the presence or absence of the indicated compounds (10 μM) during a week. After that, NS from 10-day old cultures were plated for 72 hours onto 100 μg/mL poly-L-lysine-coated coverslips in the absence of exogenous growth factors.

Immunocytochemistry

Neurogenesis is a crucial property for new AD-modifying drugs, since it confers the potential to increase endogenous regeneration as a repair mechanism in the damaged brain, and reduce neuronal loss and degeneration. Considering that GSK-3β inhibition is reported to regulate and increase neurogenesis [Lange, C.; Mix, E.; Frahm, J.; Glass, A.; Muller, J.; Schmitt, O.; Schmole, A. C.; Klemm, K.; Ortinau, S.; Hubner, R.; Frech, M. J.; Wree, A.; Rolfs, A. Small molecule GSK-3 inhibitors increase neurogenesis of human neural progenitor cells. Neurosci. Lett. 2011, 488, 36-40; Morales-Garcia, J. A.; Luna-Medina, R.; Alonso-Gil, S.; Sanz-SanCristobal, M.; Palomo, V.; Gil, C.; Santos, A.; Martinez, A.; Perez-Castillo, A. Glycogen Synthase Kinase 3 Inhibition Promotes Adult Hippocampal Neurogenesis in Vitro and in Vivo. ACS Chem. Neurosci. 2012, 3, 963-971], it was on interest to verify whether addition of compounds of example 3 and 6 to NS cultures of primary rat neural stem cells could regulate cell differentiation toward a neuronal phenotype. Thus, cells were processed for immunocytochemistry to detect neural markers, such as β-tubulin and the microtule-associated protein (MAP2), which demonstrate the potential neurogenic effect of the compounds of the invention.

Cells were processed for immunocytochemistry as previously described [Luna-Medina, R.; Cortes-Canteli, M.; Alonso, M.; Santos, A.; Martinez, A.; Perez-Castillo, A. Regulation of inflammatory response in neural cells in vitro by thiadiazolidinones derivatives through peroxisome proliferator-activated receptor gamma activation. J. Biol. Chem. 2005, 280, 21453-21462]. Briefly, at the end of the treatment period, NS cultures were grown on glass coverslips in 24-well cell culture plates. Cultures were then washed with phosphate-buffered saline (PBS) and fixed for 30 minutes with 4% paraformaldehyde at 25° C. and permeabilized with 0.1% Triton X-100 for 30 minutes at 37° C. After 1 hour incubation with the selected primary antibodies (polyclonal anti-β-tubulin (clone Tuj1; Abcam) and mouse monoclonal anti-MAP2 (Sigma)) cells were washed with phosphate-buffered saline and incubated with the corresponding Alexa-labeled secondary antibody (Alexa-488 and Alex-647 to reveal β-tubulin and MAP2 respectively; Molecular Probes; Leiden, The Netherlands) for 45 minutes at 37° C. Later on, images were obtained using a TCS SP5 laser scanning spectral confocal microscope (Leica Microsystems). Confocal microscope settings were adjusted to produce the optimum signal-to-noise ratio. Dapi staining was used as a nuclear marker.

Figure 3:
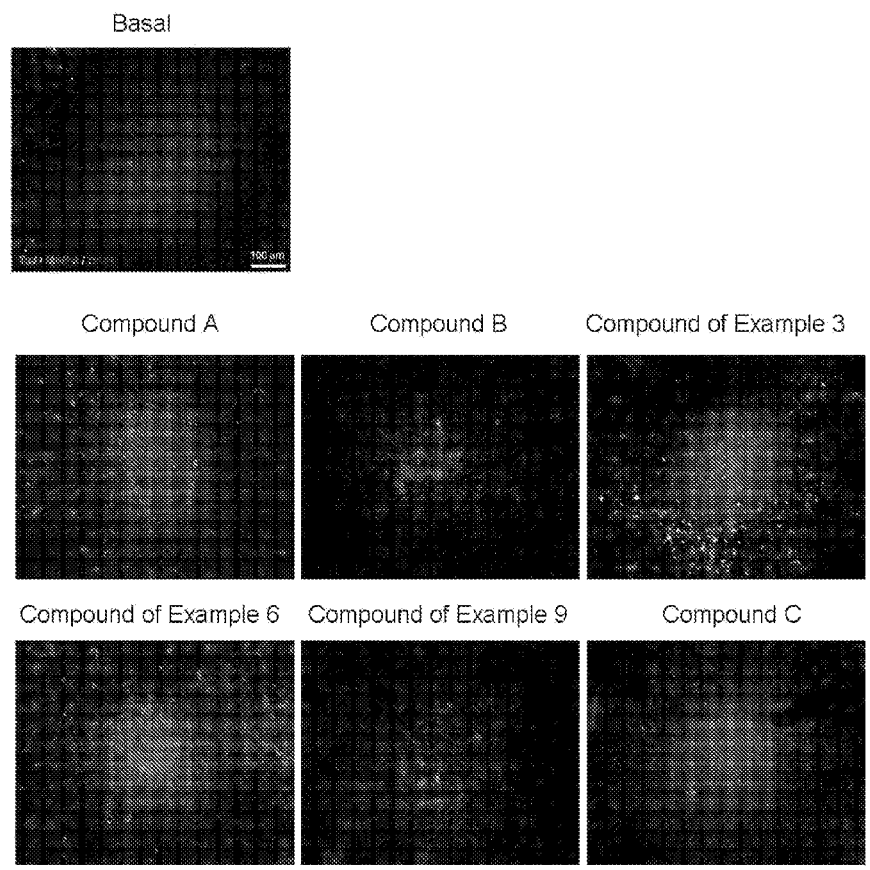

As shown in FIG. 3, some neurogenic effects were observed when neurospheres were treated with triazinones. Particularly, when compared to control, the number of β-tubulin positive cells (immature neuronal marker) was significantly increased in cultures treated with compound of example 3. Notably, compound of example 6 significantly amplified the number of MAP-2 positive cells (mature neuronal marker), whereas only a marginal increase was appreciable in cells treated with the reference compound A.

Methods to Assess the Neurotoxic Effects and the Glial Modulatory Activity of the Compounds of the Invention Primary Cell Cultures Mixed glial cell cultures were prepared from cerebral cortex of newborn Wistar rats (*Rattus norvegicus*), as previously described [Monti, B.; D'Alessandro, C.; Farini, V.; Bolognesi, A.; Polazzi, E.; Contestabile, A.; Stirpe, F.; Battelli, M. G. In vitro and in vivo toxicity of type 2 ribosome-inactivating proteins lanceolin and stenodactylin on glial and neuronal cells. Neurotoxicology 2007, 28, 637-644]. Briefly, brain tissue was cleaned from meninges, trypsinized for 15 minutes at 37° C. and, after mechanical dissociation, the cell suspension was washed and plated on poly-L-lysine (Sigma-Aldrich, St. Louis, Mo., USA, 10 µg/mL) coated flasks (75 cm$^2$). Mixed glial cells were cultured for 10-13 days in Basal Medium Eagle (BME, Life technologies Ltd, Paisley, UK) supplemented with 100 mL/L heat-inactivated FBS (Life technologies), 2 mmol/L glutamine (Sigma-Aldrich) and 100 µmol/L gentamicin sulfate (Sigma-Aldrich).

Microglial cells were harvested from mixed glial cell cultures by mechanical shaking, resuspended in fresh medium without serum and plated on uncoated 35 mm Ø dishes at a density of $1.5 \times 10^6$ cells/1.5 mL medium/well for western blot analysis or on 96 wells at $1 \times 10^5$ cells/0.2 mL medium/well for MTT assay. Cells were allowed to adhere for 30 minutes and then washed to remove non-adhering cells. These primary cultures are pure microglial cells, being more than 99% of adherent cells positive for isolectin B4 and negative for astrocyte and oligodendrocyte markers.

For the preparation of purified astrocyte cultures, 10-day-old primary mixed glial cultures were vigorously shaken to detach microglia and oligodendrocytes growing on top of the astrocytic layer. The remaining adherent cells were detached with trypsin (0.25%)/EDTA (Life technologies), and the resulting cell suspension was left at rt in uncoated flasks to allow adherence of microglia to the plastic surface. After 20-30 minutes, non-adherent or loosely adherent cells were collected after mild shaking of the flasks, and the adhesion step was performed once more. Supernatants containing non-adherent cells were collected and centrifuged; cells were resuspended in fresh BME medium without serum (Life technologies) and reseeded on poly-L-lysine-coated (Sigma-Aldrich) 35 mm Ø dishes at a density of $1.5 \times 10^6$ cells/1.5 mL medium/well for western blot analysis or on 96 wells at $1 \times 10^5$ cells/0.2 mL medium/well for MTT assay. Afterwards, western blot analysis was performed.

Primary cultures of cerebellar granular neurons (CGNs) were prepared from 7 day-old rats of Wistar strain, as previously described [Monti, B.; D'Alessandro, C.; Farini, V.; Bolognesi, A.; Polazzi, E.; Contestabile, A.; Stirpe, F.; Battelli, M. G. In vitro and in vivo toxicity of type 2 ribosome-inactivating proteins lanceolin and stenodactylin on glial and neuronal cells. Neurotoxicology 2007, 28, 637-644]. Briefly, cells were dissociated from cerebella and plated on 35 Ø mm dishes or in 24 well plates, previously coated with 10 µg/mL poly-L-lysine, at a density of $2 \times 10^5$ cells/cm$^2$ in BME supplemented with 100 mL/L heat-inactivated FBS (Life technologies), 2 mmol/L glutamine, 100 µmol/L gentamicin sulphate and 25 mmol/L KCl (all from Sigma-Aldrich). 16 hours later, 10 µM cytosine arabinofuranoside (Sigma-Aldrich) was added to avoid glial proliferation. After 7 days in vitro (7 DIV), differentiated neurons were shifted to serum free BME medium containing 25 mmol/L KCl and used for MTT assay.

MTT Assay

The viability of the different brain cells in primary cultures exposed to increasing concentrations of compounds of example 3 and 6 (0, 10, 20 and 50 µM) for 24 hours was evaluated by MTT assay [Monti, B.; D'Alessandro, C.; Farini, V.; Bolognesi, A.; Polazzi, E.; Contestabile, A.; Stirpe, F.; Battelli, M. G. In vitro and in vivo toxicity of type 2 ribosome-inactivating proteins lanceolin and stenodactylin on glial and neuronal cells. Neurotoxicology 2007, 28, 637-44]. Briefly, thiazolyl blue was added to culture medium at a final concentration of 0.1 mg/mL. Following a 20 minutes incubation for CGNs and 2 hours for glial cells at 37° C. in the dark, the MTT precipitate was dissolved in 0.1 M Tris-HCl buffer containing 5% Triton X-100 (all from Sigma-Aldrich) and absorbance was read at 570 nm in a multiplate spectophotometric reader (Bio-Rad).

Figure 4:
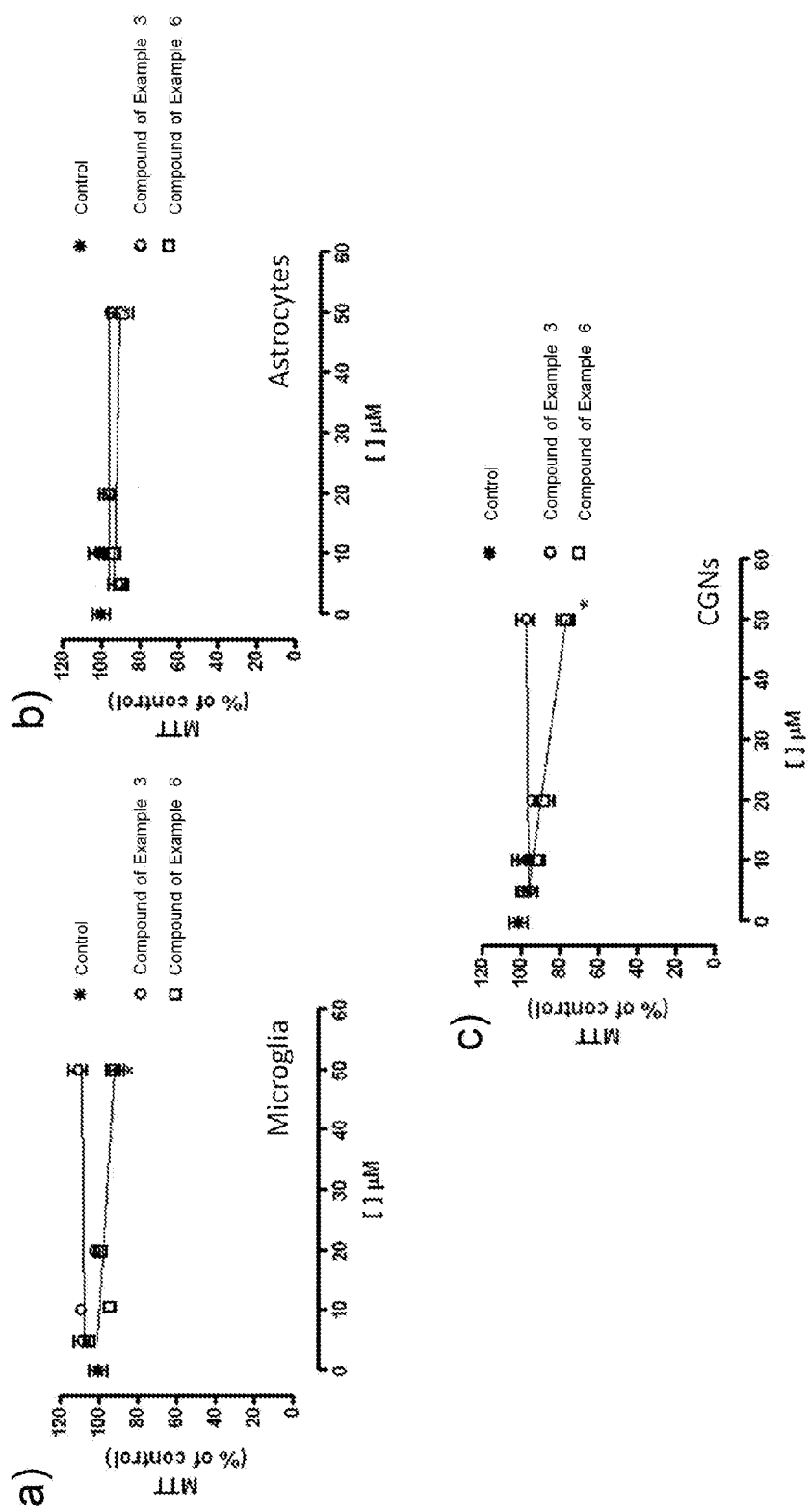

Importantly, compounds of example 3 and 6 did not display any toxicity in glial and neuronal cells up to 50 µM (FIGS. 4a, 4b and 4c).

Western Blot Analysis.

The transformation from the neuroprotective M2 to the cytotoxic M1 glial cells is considered a crucial step in the progression of AD [Boche, D.; Perry, V. H.; Nicoll, J. A. Review: activation patterns of microglia and their identification in the human brain. Neuropathol. Appl. Neurobiol. 2013, 39, 3-18]. This M1/M2 phenotypic classification is based on a specific pattern of pro- or anti-inflammatory cytokines and receptors, whose release and expression is regulated, among others, by GSK-3β activity [Goldmann, T.; Prinz, M. Role of microglia in CNS autoimmunity. Clin. Dev. Immunol. 2013, 2013, 208093]. In this respect, GSK-3β activation has been reported to foster and maintain the pro-inflammatory state. On this basis, we evaluated the ability of compounds of example 3 and 6 to modulate the expression level of the inducible nitric oxide synthase (iNOS) as M1 marker, and the triggering receptor expressed on myeloid cells 2 (TREM2) as M2 marker on glial cells.

Microglial and astrocyte cells exposed to LPS (100 ng/mL) in presence or absence of different concentrations (0, 5, 10 and 20 µM) of compounds of example 3 and 6 for 24 hours were directly in ice-cold lysis buffer (Tris 50 mM, SDS 1%, protease inhibitor cocktail 0.05%) and protein content was determined by using the Lowry method [Lowry, O. H.; Rosebrough, N. J.; Farr, A. L.; Randall, R. J. Protein measurement with the Folin phenol reagent. J. Biol. Chem. 1951, 193, 265-275]. 20 µg of protein extracts were resuspended in 20 µL of loading buffer (0.05M Tris-HCl pH 6.8; 40 g/L sodium dodecyl sulfate; 20 mL/L glycerol; 2 g/L bromophenol blue and 0.02 M dithiothreitol; all chemicals were from Sigma-Aldrich) and loaded onto 10% sodium dodecyl sulfate-polyacrylamide gels (SDS-PAGE; Bio-Rad Laboratories SrL, Segrate, MI, IT). After electrophoresis and transfer onto nitrocellulose membranes (GE Healthcare Europe GmbH, Milano, MI, IT), membranes were blocked for 1 hour in 5% non-fat milk (Bio-Rad)/0.1% Tween-20 in phosphate buffered saline (PBS, Sigma-Aldrich), pH 7.4, and incubated overnight) at 4° C. with primary antibodies (rabbit polyclonal anti-iNOS or anti-TREM2 1:1000, both from Santa Cruz Biotechnology Inc., Santa Cruz, Calif., USA, or mouse monoclonal anti-βactin, 1:2000, Sigma-Aldrich) in 0.1% Tween-20/PBS. Membranes were then incubated with an anti-rabbit or anti-mouse secondary antibody conjugated to horseradish peroxidase (1:2000; Santa Cruz), for 90 minutes at rt in 0.1% Tween-20/PBS. Labelled proteins were detected by using the enhanced chemiluminescence method (ECL; Bio-RAD). Densitometric analysis was performed by using Scion Image software from NIH.

Figure 5:
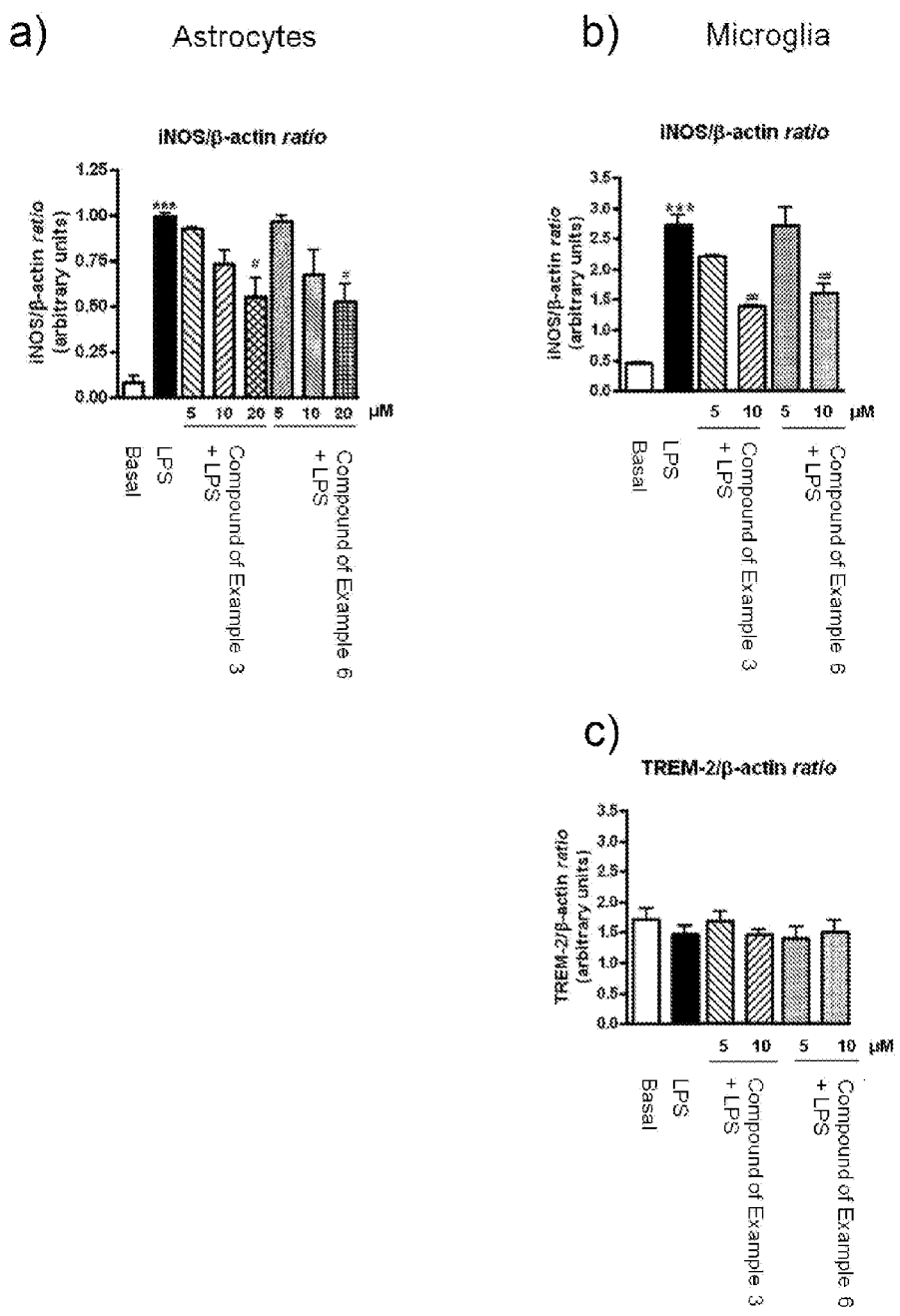

As shown in FIG. 5, when cultures of primary rat glial cells were stimulated with LPS, we observed the expected iNOS induction, which was reduced by a 24 hours co-treatment with compounds of example 3 and 6 in a dose-dependent manner (FIGS. 5a and b). Furthermore, along the same line, in microglia cells treated with LPS we observed a reduction of TREM2 expression, which was restored by 24 hours co-treatment with compounds of example 3 and 6 (FIG. 5c).

TABLE 2

| Entry | Structure |
|---|---|
| Compound A | 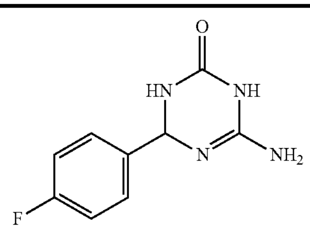 |
| Compound B | 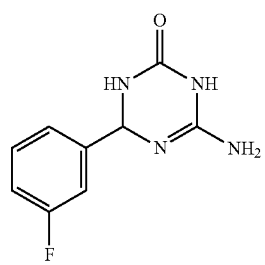 [SMILES: NC1=NC(c2cccc(F)c2)NC(=O)N1] |
| Compound C | 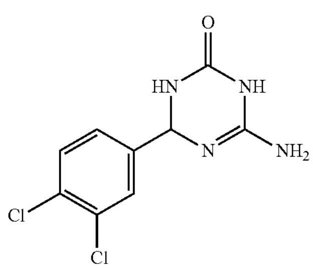 [SMILES: NC1=NC(c2ccc(Cl)c(Cl)c2)NC(=O)N1] |

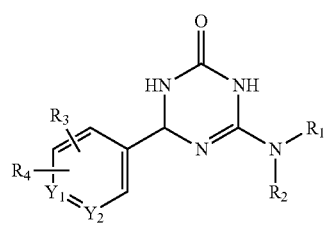

The invention claimed is:

1. A compound of Formula (I)

(I)

wherein:
R$_1$ is hydrogen or linear C$_{1-6}$alkyl, unsubstituted or substituted with one or more R$_6$ substituents;
R$_2$ is selected from the group consisting of linear or branched C$_{1-6}$alkyl, unsubstituted or substituted with one or more R$_6$ substituents; C$_{3-6}$cycloalkyl, unsubstituted or substituted with one or more R$_6$ substituents; C$_{3-6}$cycloalkylC$_{1-6}$alkyl, unsubstituted or substituted with one or more R$_6$ substituents; aryl, unsubstituted or substituted with one or more R$_6$ substituents; heteroaryl, unsubstituted or substituted with one or more R$_6$ substituents; arylC$_{1-6}$alkyl, unsubstituted or substituted with one or more R$_6$ substituents; aryloxyC$_{1-6}$alkyl, unsubstituted or substituted with one or more R$_6$ substituents; heteroarylC$_{1-6}$alkyl, unsubstituted or substituted with one or more R$_6$ substituents; heteroaryloxyC$_{1-6}$alkyl, unsubstituted or substituted with one or more R$_6$ substituents; heterocycloalkylC$_{1-6}$alkyl, unsubstituted or substituted with one or more R$_6$ substituents; or COR$_5$;
R$_5$ is selected from the group consisting of linear or branched C$_{1-9}$alkyl, unsubstituted or substituted with one or more R$_6$ substituents; C$_{3-6}$cycloalkyl, unsubstituted or substituted with one or more R$_6$ substituents; C$_{3-6}$cycloalkylC$_{1-6}$alkyl, unsubstituted or substituted with one or more R$_6$ substituents; aryl, unsubstituted or substituted with one or more R$_6$ substituents; heteroaryl, unsubstituted or substituted with one or more R$_6$ substituents; arylC$_{1-6}$alkyl, unsubstituted or substituted with one or more R$_6$ substituents; aryloxyC$_{1-6}$alkyl, unsubstituted or substituted with one or more R$_6$ substituents; heteroarylC$_{1-6}$alkyl, unsubstituted or substituted with one or more R$_6$ substituents; heteroaryloxyC$_{1-6}$alkyl, unsubstituted or substituted with one or more R$_6$ substituents; heterocycloalkylC$_{1-6}$alkyl, unsubstituted or substituted with one or more R$_6$ substituents;
R$_6$ is selected from the group consisting of halogen and dialkylamino;
or, R$_1$ and R$_2$ together with the nitrogen atom to which they are attached may form a 4- to 7-membered azacyclic ring containing up to two nitrogen atoms;
Y$_1$ and Y$_2$ are independently selected from C or N;
R$_3$ and R$_4$ are independently selected from the group consisting of hydrogen, halogen, linear or branched unsubstituted or substituted C$_{1-6}$alkyl, unsubstituted or substituted C$_{1-6}$alkoxy, hydroxy, trifluoromethyl, amino, monoalkylamino, dialkylamino,
or a pharmaceutically acceptable salt or solvate thereof.

2. The compound according to claim 1, wherein:
R$_1$ is hydrogen or linear C$_{1-4}$alkyl, unsubstituted or substituted with one or more R$_6$ substituents;
R$_2$ is selected from the group consisting of linear or branched C$_{1-4}$alkyl, unsubstituted or substituted with one or more R$_6$ substituents; C$_{3-6}$cycloalkyl, unsubstituted or substituted with one or more R$_6$ substituents; C$_{3-6}$cycloalkylC$_{1-4}$alkyl, unsubstituted or substituted with one or more R$_6$; aryl, unsubstituted or substituted with one or more R$_6$ substituents; heteroaryl, unsubstituted or substituted with one or more R$_6$ substituents; arylC$_{1-4}$alkyl, unsubstituted or substituted with one or more R$_6$ substituents; heteroarylC$_{1-4}$alkyl, unsubstituted or substituted with one or more R$_6$ substituents; heterocycloalkylC$_{1-4}$alkyl, unsubstituted or substituted with one or more R$_6$ substituents; and COR$_5$;
R$_5$ is selected from the group consisting of linear or branched C$_{1-7}$alkyl, unsubstituted or substituted with one or more R$_6$ substituents; arylC$_{1-4}$alkyl, unsubstituted or substituted with one or more R$_6$ substituents; aryloxyC$_{1-4}$alkyl, unsubstituted or substituted with one or more R$_6$ substituents; heteroarylC$_{1-4}$alkyl, unsubstituted or substituted with one or more R$_6$ substituents; heteroaryloxyC$_{1-4}$alkyl, unsubstituted or substituted with one or more R$_6$ substituents; heterocyclylC$_{1-4}$alkyl, unsubstituted or substituted with one or more R$_6$ substituents;

$R_6$ is selected from the group consisting of halogen and dialkylamino;

or, $R_1$ and $R_2$ together with the nitrogen atom to which they are attached may form a 4- to 6-membered azacyclic ring containing one nitrogen atom;

$Y_1$ and $Y_2$ are independently selected from C or N;

$R_3$ and $R_4$ are independently selected from the group consisting of hydrogen, halogen, linear or branched unsubstituted or substituted $C_{1-3}$alkyl, unsubstituted or substituted $C_{1-3}$alkoxy, hydroxy, trifluoromethyl.

3. The compound according to claim 1 wherein:

$R_1$ is hydrogen, methyl, ethyl, and n-propyl unsubstituted or substituted with one $R_6$ substituent;

$R_2$ is selected from the group consisting of methyl, ethyl, n-propyl, i-propyl, n-butyl, i-butyl, cyclopropyl, cyclopropylmethyl, phenyl, benzyl, 4-pyridylmethyl, piperidin-1-ylpropyl, morpholin-4-yl-propyl, 4-methylpiperazin-1-yl-propyl, $COR_5$;

$R_5$ is selected from the group consisting of methyl, ethyl, n-propyl, i-propyl, i-butyl, 1-propylbutyl, phenoxymethyl unsubstituted or substituted with one $R_6$ substituent, heteroaryloxyethyl unsubstituted or substituted with one $R_6$ substituent, heterocycloalkylbutyl unsubstituted or substituted with one $R_6$ substituent;

$R_6$ is selected from the group consisting of fluorine and dialkylamino group;

or, $R_1$ and $R_2$ together with the nitrogen atom to which they are attached may form an azacyclic ring selected from an azetidine, a pyrrolidine or a piperidine ring system;

$Y_1$ and $Y_2$ are independently selected from C or N;

$R_3$ and $R_4$ are independently selected from the group consisting of hydrogen, fluorine, methyl.

4. A compound selected from the group consisting of:

4-(4-fluorophenyl)-6-(methylamino)-3,4-dihydro-1,3,5-triazin-2(1H)-one;

6-(ethylamino)-4-(o-tolyl)-3,4-dihydro-1,3,5-triazin-2(1H)-one;

6-(ethylamino)-4-(4-fluorophenyl)-3,4-dihydro-1,3,5-triazin-2(1H)-one;

6-(ethylamino)-4-(4-fluorophenyl)-3,4-dihydro-1,3,5-triazin-2(1H)-one;

6-(ethylamino)-4-(4-fluorophenyl)-3,4-dihydro-1,3,5-triazin-2(1H)-one;

4-(4-fluorophenyl)-6-(propylamino)-3,4-dihydro-1,3,5-triazin-2(1H)-one;

4-(4-fluorophenyl)-6-(isopropylamino)-3,4-dihydro-1,3,5-triazin-2(1H)-one;

4-(4-fluorophenyl)-6-(isobutylamino)-3,4-dihydro-1,3,5-triazin-2(1H)-one;

4-(4-fluorophenyl)-6-(phenylamino)-3,4-dihydro-1,3,5-triazin-2(1H)-one;

6-(dimethylamino)-4-(4-fluorophenyl)-3,4-dihydro-1,3,5-triazin-2(1H)-one;

6-(diethylamino)-4-(4-fluorophenyl)-3,4-dihydro-1,3,5-triazin-2(1H)-one;

4-(4-fluorophenyl)-6-(piperidin-1-yl)-3,4-dihydro-1,3,5-triazin-2(1H)-one;

6-(butylamino)-4-(4-fluorophenyl)-3,4-dihydro-1,3,5-triazin-2(1H)-one;

6-(ethylamino)-4-(pyridin-3-yl)-3,4-dihydro-1,3,5-triazin-2(1H)-one;

4-(4-fluorophenyl)-6-(pyrrolidin-1-yl)-3,4-dihydro-1,3,5-triazin-2(1H)-one;

N-(4-(4-fluorophenyl)-6-oxo-1,4,5,6-tetrahydro-1,3,5-triazin-2-yl)acetamide;

N-(4-(4-fluorophenyl)-6-oxo-1,4,5,6-tetrahydro-1,3,5-triazin-2-yl)-2-propylpentanamide;

5-(1,2-dithiolan-3-yl)-N-(4-(4-fluorophenyl)-6-oxo-1,4,5,6-tetrahydro-1,3,5-triazin-2-yl)pentanamide;

3-((1H-benzo[d][1,2,3]triazol-1-yl)oxy)-N-(4-(4-fluorophenyl)-6-oxo-1,4,5,6-tetrahydro-1,3,5-triazin-2-yl)propanamide;

N-(4-(4-fluorophenyl)-6-oxo-1,4,5,6-tetrahydro-1,3,5-triazin-2-yl)-2-phenoxyacetamide;

2-(4-fluorophenoxy)-N-(4-(4-fluorophenyl)-6-oxo-1,4,5,6-tetrahydro-1,3,5-triazin-2-yl)acetamide;

6-((3-(dimethylamino)propyl)amino)-4-(4-fluorophenyl)-3,4-dihydro-1,3,5-triazin-2(1H)-one;

4-(4-fluorophenyl)-6-((3-(piperidin-1-yl)propyl)amino)-3,4-dihydro-1,3,5-triazin-2(1H)-one;

6-(benzylamino)-4-(4-fluorophenyl)-3,4-dihydro-1,3,5-triazin-2(1H)-one;

4-(4-fluorophenyl)-6-((pyridin-4-ylmethyl)amino)-3,4-dihydro-1,3,5-triazin-2(1H)-one;

6-(dipropylamino)-4-(4-fluorophenyl)-3,4-dihydro-1,3,5-triazin-2(1H)-one, 6-(cyclopropylamino)-4-(4-fluorophenyl)-3,4-dihydro-1,3,5-triazin-2(1H)-one;

6-((cyclopropylmethyl)amino)-4-(4-fluorophenyl)-3,4-dihydro-1,3,5-triazin-2(1H)-one;

6-((3-(diethylamino)propyl)amino)-4-(4-fluorophenyl)-3,4-dihydro-1,3,5-triazin-2(1H)-one;

4-(4-fluorophenyl)-6-((3-morpholinopropyl)amino)-3,4-dihydro-1,3,5-triazin-2(1H)-one;

4-(4-fluorophenyl)-6-((3-(4-methylpiperazin-1-yl)propyl)amino)-3,4-dihydro-1,3,5-triazin-2(1H)-one;

6-(azetidin-1-yl)-4-(4-fluorophenyl)-3,4-dihydro-1,3,5-triazin-2(1H)-one;

N-(4-(4-fluorophenyl)-6-oxo-1,4,5,6-tetrahydro-1,3,5-triazin-2-yl)propionamide;

N-(4-(4-fluorophenyl)-6-oxo-1,4,5,6-tetrahydro-1,3,5-triazin-2-yl)butyramide;

N-(4-(4-fluorophenyl)-6-oxo-1,4,5,6-tetrahydro-1,3,5-triazin-2-yl)isobutyramide;

N-(4-(4-fluorophenyl)-6-oxo-1,4,5,6-tetrahydro-1,3,5-triazin-2-yl)-3-methylbutanamide.

5. Pharmaceutical composition comprising a compound of Formula (I) according to claim 1 and a pharmaceutically acceptable carrier, stabilizer, diluent, or excipient thereof.

6. The pharmaceutical composition according to claim 5 further comprising a second therapeutic agent.

7. The pharmaceutical composition according to claim 5 wherein the second therapeutic agent is selected from the group consisting of a neuroprotectant and an agent for Alzheimer's disease treatment.

8. A method of treating a central nervous system disease or disorder by dual inhibition of BACE-1 and GSK-3β comprising administrating a therapeutically effective amount of a compound of Formula (I) to an individual in need thereof,

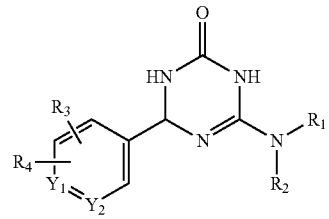

wherein:
R₁ is hydrogen, linear or branched, unsubstituted or substituted, $C_{1-6}$ alkyl;
R₂ is selected from the group consisting of linear or branched, unsubstituted or substituted, $C_{1-6}$alkyl, $C_{2-6}$alkenyl, $C_{2-6}$alkynyl, unsubstituted or substituted $C_{3-6}$cycloalkyl, unsubstituted or substituted $C_{3-6}$cycloalkyl$C_{1-6}$ alkyl, unsubstituted or substituted aryl, unsubstituted or substituted heteroaryl, unsubstituted or substituted aryl $C_{1-6}$alkyl, unsubstituted or substituted aryloxy$C_{1-6}$alkyl, unsubstituted or substituted heteroaryl$C_{1-6}$alkyl, unsubstituted or substituted heteroaryloxy$C_{1-6}$alkyl, unsubstituted or substituted heterocycloalkyl$C_{1-6}$alkyl, COR₅;
R₅ is selected from the group consisting of linear or branched unsubstituted or substituted $C_{1-9}$alkyl, unsubstituted or substituted $C_{3-6}$cycloalkyl, unsubstituted or substituted $C_{3-6}$cycloalkyl$C_{1-6}$alkyl, unsubstituted or substituted aryl, unsubstituted or substituted heteroaryl, unsubstituted or substituted aryl$C_{1-6}$alkyl, unsubstituted or substituted aryloxy$C_{1-6}$alkyl, unsubstituted or substituted heteroaryl$C_{1-6}$alkyl, unsubstituted or substituted heteroaryloxy$C_{1-6}$alkyl, unsubstituted or substituted heterocycloalkyl$C_{1-6}$alkyl;

or R₁ and R₂ together with the nitrogen atom to which they are attached may form a 4- to 7-membered azacyclic ring containing up to three heteroatoms selected from nitrogen and oxygen;
Y₁ and Y₂ are independently selected from C or N;
R₃ and R₄ are independently selected from the group consisting of hydrogen, halogen, linear or branched unsubstituted or substituted $C_{1-6}$alkyl, unsubstituted or substituted $C_{1-6}$alkoxy, unsubstituted or substituted hydroxy$C_{1-6}$alkyl, hydroxy, cyano, nitro, unsubstituted or substituted fluoro$C_{1-6}$alkyl, unsubstituted or substituted fluoro$C_{1-6}$alkoxy, amino, monoalkylamino, dialkylamino;
or pharmaceutically acceptable salt or solvate thereof;
wherein the disease or condition is selected from the group consisting of Alzheimer's diseases, AIDS-related dementia, cancer-related dementia, frontotemporal dementia, inflammation and chronic inflammatory diseases, and tauopathies.

9. The pharmaceutical composition according to claim 7 wherein the second therapeutic agent is selected from the group consisting of galantamine, rivastigmine, donepezil, and memantine.

* * * * *

UNITED STATES PATENT AND TRADEMARK OFFICE
CERTIFICATE OF CORRECTION

PATENT NO. : 9,975,861 B2
APPLICATION NO. : 15/316883
DATED : May 22, 2018
INVENTOR(S) : Andrea Cavalli et al.

Page 1 of 1

It is certified that error appears in the above-identified patent and that said Letters Patent is hereby corrected as shown below:

On the Title Page

At item (73), Line 1, "ITAIANO" should be -- ITALIANO --.

Signed and Sealed this
Thirtieth Day of July, 2019

Andrei Iancu
*Director of the United States Patent and Trademark Office*